US012790652B2

(12) United States Patent
Nanayakkara et al.

(10) Patent No.: US 12,790,652 B2
(45) Date of Patent: Nov. 10, 2026

(54) UNIVERSAL PRIMERS FOR RAPID BACTERIAL GENOME DETECTION

(71) Applicant: BIOMERIEUX, Marcy-l'Etoile (FR)

(72) Inventors: Imaly A. Nanayakkara, Brookline, MA (US); Thomas Culp, Cambridge, MA (US); Chiahao Tsui, Somerville, MA (US); Douglas S. Kwon, Somerville, MA (US)

(73) Assignee: bioMerieux, Marcy L'Etoile (FR)

( * ) Notice: Subject to any disclaimer, the term of this patent is extended or adjusted under 35 U.S.C. 154(b) by 433 days.

(21) Appl. No.: 18/038,248

(22) PCT Filed: Nov. 19, 2021

(86) PCT No.: PCT/US2021/060028
§ 371 (c)(1),
(2) Date: May 23, 2023

(87) PCT Pub. No.: WO2022/115318
PCT Pub. Date: Jun. 2, 2022

(65) Prior Publication Data

US 2023/0416845 A1 Dec. 28, 2023

Related U.S. Application Data

(60) Provisional application No. 63/117,497, filed on Nov. 24, 2020.

(51) Int. Cl.
*C12Q 1/68* (2018.01)
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS 10,544,446 B1 1/2020 Tsui
2023/0416845 A1* 12/2023 Nanayakkara ......... C12Q 1/689

FOREIGN PATENT DOCUMENTS

CN 106 434 917 A 2/2017
JP 2008 005779 A 1/2008
JP 2008 263971 A 11/2008
WO WO 2020/176822 A1 9/2020
WO WO-2022115318 A1 * 6/2022 ............ C12Q 1/689

OTHER PUBLICATIONS

Bergmark et al., 2012. Assessment of the specificity of Burkholderia and Pseudomonas qPCR assays for detection of these genera in soil using 454 pyrosequencing. FEMS microbiology letters, 333(1), pp. 77-84. (Year: 2012).*

Bemer et al., 2014. Evaluation of 16S rRNA gene PCR sensitivity and specificity for diagnosis of prosthetic joint infection: a prospective multicenter cross-sectional study. Journal of clinical microbiology, 52(10), pp. 3583-3589. (Year: 2014).*

Fukuta et al., 2013. Detection of Pythium aphanidermatum in tomato using loop-mediated isothermal amplification (LAMP) with species-specific primers. Eur journal of plant pathology, 136(4), pp. 689-701 (Year: 2013).*

Guo et al., 2008. Real-time PCR quantification of the predominant bacterial divisions in the distal gut of Meishan and Landrace pigs. Anaerobe, 14(4), pp. 224-228. (Year: 2008).*

Layton, 2006. Development of Bacteroides 16S rRNA gene TaqMan-based real-time PCR assays for estimation of total, human, and bovine fecal pollution in water. Applied and environmental microbiology, 72(6), pp. 4214-4224. (Year: 2006).*

Lin et al., 2017. Direct bacterial loop-mediated isothermal amplification detection on the pathogenic features of the nosocomial pathogen-Methicillin resistant *Staphylococcus aureus* strains with respiratory origins. Microbial Pathogenesis, 109, pp. 183-188. (Year: 2017).*

Marin et al., 2012. Role of universal 16S rRNA gene PCR and sequencing in diagnosis of prosthetic joint infection. Journal of clinical microbiology, 50(3), pp. 583-589. (Year: 2012).*

Nanayakkara, I.A. and White, I.M., 2019. Demonstration of a quantitative triplex LAMP assay with an improved probe-based readout for the detection of MRSA. Analyst, 144(12), pp. 3878-3885. (Year: 2019).*

Nagarajappa et al., 2012. Detection of enterotoxigenic staphylococci by loop-mediated isothermal amplification method. Journal of Food Safety, 32(1), pp. 59-65. (Year: 2012).*

Najafpour et al., 2022. Quantifying dominant bacterial genera detected in metagenomic data from fish eggs and larvae using genus-specific primers. Microbiology Open, 11(3), e1274, pp. 1-14 (Year: 2022).*

Sharma, A. and Gaind, R., Jun. 2021. Development of loop-mediated isothermal amplification assay for detection of clinically significant members of Acinetobacter calcoaceticus-baumannii complex and associated carbapenem resistance. Frontiers in Molecular Biosciences, 8, 659256, pp. 1-13. (Year: 2021).*

Si et al., Sep. 27, 2021. A LAMP-based system for rapid detection of eight common pathogens causing lower respiratory tract infections. Journal of Microbiological Methods, 190, 106339, pp. 1-7. (Year: 2021).*

(Continued)

*Primary Examiner* — Gary Benzion
*Assistant Examiner* — Olayinka A Oyeyemi

(57) ABSTRACT

The present disclosure relates generally to methods, compositions, and kits useful for detecting a multiplicity of bacterial genomes present in a sample (e.g., a biological sample obtained from a subject exhibiting one or more signs or symptoms of a bacterial infection). Specifically, the present disclosure relates to nucleic acid primers, primer sets, and multiplicities of primer sets that allow for broad (e.g., species non-specific) detection of bacterial genomes present in such a sample using loop-mediated isothermal amplification (LAMP).

19 Claims, 12 Drawing Sheets

Specification includes a Sequence Listing.

(56) References Cited

OTHER PUBLICATIONS

Sonaty, G.T., 2015. Multiplexed microfluidic loop-mediated isothermal amplification of the 16s rRNA gene for the diagnosis of neonatal sepsis in resource-limited environments. pp. 1-21, Undergraduate Honors Theses from Dept of BioEngineering, U. Arkansas, Fayetteville. (Year: 2015).*

Vijayakumar et al., 2019. Accurate identification of clinically important *Acinetobacter* spp.: an update. Future science OA, 5(6), FSO395. (Year: 2019).*

Wang et al., 2013. Real-time fluorescence loop mediated isothermal amplification for the detection of Acinetobacter baumannii. PloS one, 8(7), e66406, pp. 1-7. (Year: 2013).*

Wang et al., 2015. Development of primer sets for loop-mediated isothermal amplification that enables rapid and specific detection of *Streptococcus dysgalactiae, Streptococcus uberis* and *Streptococcus agalactiae*. International Journal of Environmental Research and Public Health, 12(6), pp. 5735-5742. (Year: 2015).*

Yang et al., 2016. Two multiplex real-time PCR assays to detect and differentiate Acinetobacter baumannii and non-*Baumannii Acinetobacter* spp. carrying bla NDM, bla OXA-23-like, bla OXA-40-like, bla OXA-51-like, and bla OXA-58-like genes. PloS one, 11(7), e0158958, pp. 1-13. (Year: 2016).*

Zhang et al., 2015. Application of loop-mediated isothermal amplification (LAMP) assay for the rapid diagnosis of pathogenic bacteria in clinical sputum specimens of acute exacerbation of COPD (AECOPD). International Journal of Clinical and Experimental Medicine, 8(5), p. 7881-7889. (Year: 2015).*

Xu et al., 2012. Development and application of loop-mediated isothermal amplification assays on rapid detection of various types of staphylococci strains. Food Research International, 47(2), pp. 166-173. (Year: 2012).*

Invitation to Pay Additional Fees for International Application No. PCT/US2021/060028 mailed Mar. 4, 2022.

International Search Report and Written Opinion for International Application No. PCT/US2021/060028 mailed Apr. 29, 2022.

International Preliminary Report on Patentability for International Application No. PCT/US2021/060028 mailed Jun. 8, 2023.

Adekambi et al., The rpoB gene as a tool for clinical microbiologists. Cell. Jan. 2009;17(1): 37-45. doi.org/10.1016/j.tim.2008.09.008.

Jiang et al., Robust Strand Exchange Reactions for the Sequence-Specific, Real-Time Detection of Nucleic Acid Amplicons. Anal Chem. Mar. 17, 2015;87(6):3314-20. doi: 10.1021/ac504387c. Epub Mar. 2, 2015.

Ludwig et al., Bacterial phylogeny based on 16S and 23S rRNA sequence analysis. FEMS Microbiol Rev. Oct. 1994;15(2-3):155-73. doi: 10.1111/j.1574-6976.1994.tb00132.x.

Notomi et al., Loop-mediated isothermal amplification of DNA. Nucleic Acids Res. Jun. 15, 2000;28(12):E63. doi: 10.1093/nar/28.12.e63.

Sugawara et al., Rapid and reliable detection of phytoplasma by loop-mediated isothermal amplification targeting a housekeeping gene. J. Gen. Plant Pathol. Apr. 16, 2012;78(6):389-97. doi:10.1007/s10327-012-0403-9.

Wood et al., Kraken: ultrafast metagenomic sequence classification using exact alignments, Genome Biol. Mar. 3, 2014;15(R46):1-12. doi.org/10.1186/GB-2014-15-3-r46.

Adékambi et al., The rpoB gene as a tool for clinical microbiologists. Trends Microbiol. Jan. 2009;17(1):37-45. doi: 10.1016/j.tim.2008.09.008. Epub Dec. 10, 2008.

Zhou et al., [16S rRNA gene in community structure analysis and the optimized amplification—a review]. Wei Sheng Wu Xue Bao. Jan. 2010;50(1):7-14. Chinese.

* cited by examiner

UNIVERSAL PRIMERS FOR RAPID BACTERIAL GENOME DETECTION

CROSS REFERENCE TO RELATED APPLICATIONS

This application is a national stage filing under 35 U.S.C. 371 of International Patent Application Serial No. PCT/US2021/060028, filed Nov. 19, 2021, entitled "UNIVERSAL PRIMERS FOR RAPID BACTERIAL GENOME DETECTION", which claims priority to U.S. provisional Application No. 63/117,497, filed Nov. 24, 2020, the content of which is herein incorporated by reference in its entirety.

SEQUENCE LISTING

This application contains a Sequence Listing which has been submitted in ASCII format via EFS-Web and is hereby incorporated by reference in its entirety. Said ASCII copy, created on Apr. 10, 2023, is named D081970003US01-SEQ-EMB and is 6,903 bytes in size.

FIELD OF THE INVENTION

The present disclosure relates generally to methods, compositions, and kits useful for detecting a multiplicity of bacterial genomes present in a sample (e.g., a biological sample obtained from a subject exhibiting one or more signs or symptoms of a bacterial infection). Specifically, the present disclosure relates to nucleic acid primers, primer sets, and multiplicities of primer sets that allow for broad (e.g., species non-specific) detection of bacterial genomes present in such a sample using loop-mediated isothermal amplification (LAMP).

BACKGROUND

Bacteremia, an infection characterized by the presence of viable bacteria, is a major healthcare concern worldwide as it often leads to sepsis, a dysregulated systemic response to infection resulting in organ dysfunction. Sepsis is one of the leading causes of death worldwide, as well as the leading cause of hospital deaths in the United States. (Rudd et al. (2020), *Lancet* 395:200-211). The high mortality and morbidity rates associated with sepsis are partly due to shortcomings in the gold standard method for diagnosis of bloodstream infections (BSIs), which relies on blood culturing. Blood culturing suffers from two major issues: slow turnaround times (TATs), which can be on the order of days (see, e.g., Rhodes et al. (2017), *Intensive Care Med.* 43:304-377), and low sensitivity, with approximately half of BSIs presenting a negative blood culture. (Opota et al. (2015), *Clin. Microbiol. Infection* 21:323-331). The slow TAT and poor sensitivity lead to delays in identifying the presence of bacteria in the blood, which in turn leads to delays in formulating appropriate therapy regimens for patients in need. Consequently, patient outcomes are negatively impacted in terms of risk of septic shock and mortality rates. (Kumar et al. (2016), *Critical Care Med.* 34:1589-1596). To alleviate this healthcare burden, faster diagnostics are desperately needed to definitively determine the presence of bacteria in blood.

To develop a rapid diagnostic test, one of the major shortcomings of blood culture must be addressed: its low sensitivity of 40-60%. (Samuel (2019), *J. App. Lab. Med.* 3:631-642). Previous reports have suggested that prior antibiotic use and the incompatibility of blood culturing with fastidious organisms account for the low sensitivity of blood culture (Samuel (2019), supra), and have shown that only 4-6% of blood cultures become positive for bacterial growth. (Lin and Boehm (2013), *ISRN Infectious Diseases* 2013:e135607; Brecher et al. (2016), *J. Hosp. Med.* 11(5): 336-40). Altogether, these numbers highlight the inability of blood culture as a diagnostic method to definitively rule out infections, thus preventing clinicians from making informed decisions regarding appropriate therapy.

To address the issue of sensitivity, clinical labs often employ molecular-based diagnostics alongside blood culture to confirm results. The current standard for molecular detection of bacteria primarily consists of polymerase chain reaction (PCR)-based assays, such as PCR (Lleo et al. (2014), *FEMS Microbiol. Lett.* 354:153-160), RT-PCR (Wang et al. (2016), *Scientific Reports* 6:1-6), qPCR (Fang et al. (2018), *Orthopaedic Surgery* 10:40-46), and nested PCR (Carroll et al. (2000), *J. Clin. Microbiol.* 38:1753-1757). Inherently, PCR protocols present advantages in TAT in comparison to blood culture; a standard PCR protocol can take roughly an hour (Bustin (2017), *Biomol. Detect. Quantif.* 12:10-14), and thus presents itself as an attractive companion diagnostic to blood culture.

Despite the benefits of PCR (e.g., increased sensitivity and a fast TAT in comparison to blood culture), an inherent limitation of this method is the need for thermocycling for target generation and detection. Thermocycling involves rotating through two to three temperatures, which requires fine temperature control and high-power demands to quickly cycle from near-boiling to lesser temperatures. These demands introduce instrumentation requirements that are inherently costly and complex to incorporate into an in vitro device. To avoid these issues, isothermal amplification methods have been developed to accomplish the same steps of primer binding and extension at a single operating temperature. Examples of these isothermal schemes include nicking enzyme amplification reaction (NEAR), nucleic acid sequence-based amplification (NASBA), and loop-mediated isothermal amplification (LAMP). These methods have become increasingly popular in the past few years. (Fakruddin et al. (2013), *J. Pharm. Bioallied Sci.* 5:245-252). Such amplification schemes allow for simplified instrumentation as demonstrated by platforms such as ID NOW™ (Abbott Laboratories, Abbott Park, IL), 3M™ Molecular Detection System (3M Company, St. Paul, MN), Alethia™ Molecular Diagnostic Platform (Meridian Bioscience, Inc., Cincinnati, OH) without sacrificing specificity or sensitivity. The schemes can also outperform PCR in specificity, sensitivity, and even speed; LAMP is able to detect single copies of bacterial genomic DNA within 30 minutes—half the time required for PCR. (Yano et al. (2007), *J. Microbiol. Methods* 68:414-420; Kim et al. (2012), *PLoS ONE* 7:e42954).

It is important to note that while isothermal amplification offers many benefits to PCR and blood culture, it shares the same shortcomings as PCR-related methods when used for bacterial species identification. Many PCR-based diagnostics leverage the specificity of designed primers to target unique regions of DNA at species- or strain-specific levels. As a platform is expanded to encompass more targets, it requires the development of a new primer set for every species being targeted in the assay. Cross-reactivity between primers and off-target amplification can quickly become prevalent issues that have negative impacts on sensitivity and specificity downstream. As a result, expansion requires significant effort and expense with each iterative design. To remove these challenges, these design constraints must be addressed. Therefore, there remains a need for a sensitive, specific, fast method for detecting bacteria in clinical samples that does not require intensive primer design and therefore high cost.

SUMMARY

The present disclosure provides methods that use loop-mediated isothermal amplification (LAMP) to detect bacterial genomes in a sample. Unlike traditional PCR and isothermal amplification methods, the present invention employs primers designed to target highly conserved regions of bacterial genomes. As a result of targeting regions that are conserved over multiple genomes, these primers enable detection of a wide number of bacteria, thus removing the need for extensive redesign upon incorporation of additional targets. It is demonstrated herein that sensitive and timely detection can be achieved using the primers and assay of the present invention, while reducing the incidence of false negatives. The methods described herein allow for the determination of the presence or absence of bacterial genomes in a clinical sample so as to substantially reduce misdiagnoses in a clinical setting, and can be used in conjunction with other enrichment protocols, including the current standard blood culturing methods.

The present invention depends, in part, upon the development of methods, compositions (e.g., primers, primer sets, and multiplicities of primer sets), and kits useful for detecting a multiplicity of bacterial genomes present in a sample (e.g., a biological sample obtained from a subject exhibiting one or more signs or symptoms of bacteremia). Specifically, the present disclosure relates to nucleic acid primers, primer sets, and multiplicities of primer sets that allow for broad (e.g., species non-specific) detection of bacterial genomes present in such a sample using loop-mediated isothermal amplification (LAMP).

Thus, aspects of the disclosure include a set of isolated nucleic acid primers suitable for LAMP and detection of a multiplicity of bacterial genomes. In some embodiments, the set is selected from the group consisting of: a set of nucleic acid primers for detection of Lactobacillales comprising four nucleotide sequences having at least 70% identity to SEQ ID NOs: 1-4, respectively; a set of nucleic acid primers for detection of *Staphylococcus* comprising four nucleotide sequences having at least 70% identity to SEQ ID NOs: 7-10, respectively; a set of nucleic acid primers for detection of *Acinetobacter* comprising four nucleotide sequences having at least 70% identity to SEQ ID NOs: 13-16, respectively; a set of nucleic acid primers for detection of Enterobacterales comprising four nucleotide sequences having at least 70% identity to SEQ ID NOs: 19-22, respectively; a set of nucleic acid primers for detection of Pasteurellales comprising four nucleotide sequences having at least 70% identity to SEQ ID NOs: 25-28, respectively; and a set of nucleic acid primers for detection of Pseudomonadales comprising four nucleotide sequences having at least 70% identity to SEQ ID NOs: 31-34, respectively.

In some embodiments, the set of nucleic acid primers for detection of Lactobacillales further comprises one or more additional nucleic acid primers comprising nucleotide sequences having at least 70% identity to SEQ ID NOs: 5 and/or 6, respectively. In some embodiments, the Lactobacillales are one or more bacterial species selected from the group consisting of: *Bacillus cereus, Enterococcus avium, Enterococcus casseliflavus, Enterococcus faecalis, Enterococcus faecium, Enterococcus gallinarum, Enterococcus raffinosus, Lactobacillus rhamnosus, Listeria monocytogenes, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and/or *Streptococcus sanguinis.*

In some embodiments, the set of nucleic acid primers for detection of *Staphylococcus* further comprises one or more additional nucleic acid primers comprising nucleotide sequences having at least 70% identity to SEQ ID NOs: 11 and/or 12, respectively. In some embodiments, the *Staphylococcus* are one or more bacterial species selected from the group consisting of: *Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans*, and/or *Staphylococcus warneri.*

In some embodiments, the set of nucleic acid primers for detection of *Acinetobacter* further comprises one or more additional nucleic acid primers comprising nucleotide sequences having at least 70% identity to SEQ ID NOs: 17 and/or 18, respectively. In some embodiments, the *Acinetobacter* are one or more bacterial species selected from the group consisting of *Acinetobacter ursingii* and/or *Acinetobacter baumannii.*

In some embodiments, the set of nucleic acid primers for detection of Enterobacterales further comprises one or more additional nucleic acid primers comprising nucleotide sequences having at least 70% identity to SEQ ID NOs: 23 and/or 24, respectively. In some embodiments, the Enterobacterales are one or more bacterial species selected from the group consisting of: *Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Klebsiella aerogenes, Klebsiella oxytoca, Klebsiella pneumoniae, Morganella morganii Pantoea agglomerans, Proteus mirabilis, Raoultella ornithinolytica, Salmonella enterica, Serratia liquefaciens*, and/or *Serratia marcescens.*

In some embodiments, the set of nucleic acid primers for detection of Pasteurellales further comprises one or more additional nucleic acid primers comprising nucleotide sequences having at least 70% identity to SEQ ID NOs: 29 and/or 30, respectively. In some embodiments, the Pasteurellales are one or more bacterial species selected from the group consisting of *Haemophilus influenzae* and/or *Pasteurella multocida.*

In some embodiments, the set of nucleic acid primers for detection of Pseudomonadales further comprises one or more additional nucleic acid primers comprising nucleotide sequences having at least 70% identity to SEQ ID NOs: 35 and/or 36, respectively. In some embodiments, the Pseudomonadales are one or more bacterial species selected from the group consisting of: *Acinetobacter ursingii, Acinetobacter baumannii, Pseudomonas aeruginosa, Pseudomonas putida*, and/or *Stenotrophomonas maltophilia.*

In some embodiments, each nucleic acid primer comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 1-36, respectively.

In some embodiments, each nucleic acid primer comprises a nucleotide sequence that does not have any consecutive nucleotide substitutions relative to SEQ ID NOs:

1-36, respectively. In some embodiments, each nucleic acid primer comprises a nucleotide sequence that does not have any nucleotide substitutions relative to SEQ ID NOs: 1-36, respectively, within the last 5, 6, or 7 nucleotides of the 3' end of the nucleotide sequence.

In some embodiments, the primers mediate amplification of one or more conserved regions of the bacterial genomes, optionally wherein the one or more conserved regions comprise a 16S, 23S, and/or rpoB gene sequence. In some embodiments, the multiplicity of bacterial genomes comprises genomes from two or more bacterial species.

Aspects of the present disclosure include a multiplicity of sets of isolated nucleic acid primers suitable for LAMP and detection of a multiplicity of bacterial genomes. In some embodiments, the multiplicity of sets comprises at least two sets of nucleic acid primers selected from the group consisting of the sets according to any embodiment of the present disclosure. In some embodiments, the multiplicity of sets further comprises one or more additional isolated nucleic acid primers suitable for LAMP and detection of a multiplicity of bacterial genomes.

In some embodiments, the multiplicity of sets of nucleic acid primers comprises at least two sets selected from the group consisting of: a set of nucleic acid primers for detection of Lactobacillales comprising four nucleotide sequences having at least 70% identity to SEQ ID NOs: 1-4, respectively; a set of nucleic acid primers for detection of *Staphylococcus* comprising four nucleotide sequences having at least 70% identity to SEQ ID NOs: 7-10, respectively; a set of nucleic acid primers for detection of *Acinetobacter* comprising four nucleotide sequences having at least 70% identity to SEQ ID NOs: 13-16, respectively; a set of nucleic acid primers for detection of Enterobacterales comprising four nucleotide sequences having at least 70% identity to SEQ ID NOs: 19-22, respectively; a set of nucleic acid primers for detection of Pasteurellales comprising four nucleotide sequences having at least 70% identity to SEQ ID NOs: 25-28, respectively; and a set of nucleic acid primers for detection of Pseudomonadales comprising four nucleotide sequences having at least 70% identity to SEQ ID NOs: 31-34, respectively.

In some embodiments, the set of nucleic acid primers for detection of Lactobacillales further comprises one or more nucleic acid primers comprising nucleotide sequences having at least 70% identity to SEQ ID NOs: 5 and/or 6, respectively. In some embodiments, the Lactobacillales are one or more bacterial species selected from the group consisting of: *Bacillus cereus, Enterococcus avium, Enterococcus casseliflavus, Enterococcus faecalis, Enterococcus faecium, Enterococcus gallinarum, Enterococcus raffinosus, Lactobacillus rhamnosus, Listeria monocytogenes, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and/or *Streptococcus sanguinis.*

In some embodiments, the set of nucleic acid primers for detection of *Staphylococcus* further comprises one or more nucleic acid primers comprising nucleotide sequences having at least 70% identity to SEQ ID NOs: 11 and/or 12, respectively. In some embodiments, the *Staphylococcus* are one or more bacterial species selected from the group consisting of: *Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans*, and/or *Staphylococcus* warneri.

In some embodiments, the set of nucleic acid primers for detection of *Acinetobacter* further comprises one or more nucleic acid primers comprising nucleotide sequences having at least 70% identity to SEQ ID NOs: 17 and/or 18, respectively. In some embodiments, the *Acinetobacter* are one or more bacterial species selected from the group consisting of *Acinetobacter ursingii* and/or *Acinetobacter baumannii.*

In some embodiments, the set of nucleic acid primers for detection of Enterobacterales further comprises one or more nucleic acid primers comprising nucleotide sequences having at least 70% identity to SEQ ID NOs: 23 and/or 24, respectively. In some embodiments, the Enterobacterales are one or more bacterial species selected from the group consisting of: *Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Klebsiella aerogenes, Klebsiella oxytoca, Klebsiella pneumoniae, Morganella morganii Pantoea agglomerans, Proteus mirabilis, Raoultella ornithinolytica, Salmonella enterica, Serratia liquefaciens*, and/or *Serratia marcescens.*

In some embodiments, the set of nucleic acid primers for detection of Pasteurellales further comprises one or more nucleic acid primers comprising nucleotide sequences having at least 70% identity to SEQ ID NOs: 29 and/or 30, respectively. In some embodiments, the Pasteurellales are one or more bacterial species selected from the group consisting of *Haemophilus influenzae* and/or *Pasteurella multocida.*

In some embodiments, the set of nucleic acid primers for detection of Pseudomonadales further comprises one or more nucleic acid primers comprising nucleotide sequences having at least 70% identity to SEQ ID NOs: 35 and/or 36, respectively. In some embodiments, the Pseudomonadales are one or more bacterial species selected from the group consisting of: *Acinetobacter ursingii, Acinetobacter baumannii, Pseudomonas aeruginosa, Pseudomonas putida*, and/or *Stenotrophomonas maltophilia.*

In some embodiments, at least one set further comprises one or more additional isolated nucleic acid primers suitable for LAMP and detection of a multiplicity of bacterial genomes. In some embodiments, each nucleic acid primer comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 1-36, respectively.

In some embodiments, the primers mediate amplification of one or more conserved regions of the bacterial genome, optionally wherein the one or more conserved regions comprise a 16S, 23S, and/or rpoB gene sequence. In some embodiments, the multiplicity of bacterial genomes comprises genomes from two or more bacterial species.

Aspects of the present disclosure include a method for detecting a multiplicity of bacterial genomes. In some embodiments, the method comprises: (a) providing a reaction mixture comprising at least one set according to any embodiment of the present disclosure, dNTPs, a DNA polymerase, and a DNA sample to be tested for the presence of bacterial nucleic acids; (b) incubating the reaction mixture under DNA polymerase reaction conditions to produce a reaction product comprising amplified bacterial nucleic acids; and (c) detecting the reaction product.

In some embodiments, the method further comprises a second reaction mixture comprising at least one set of nucleic acid primers according to any embodiment of the present disclosure, dNTPs, a DNA polymerase, and a DNA sample to be tested for the presence of bacterial nucleic acids, wherein the at least one set of the first reaction mixture differs from the at least one set of the second reaction mixture.

Aspects of the present invention include a kit comprising a multiplicity of sets of isolated nucleic acid primers suitable for LAMP and detection of a multiplicity of bacterial genomes. In some embodiments, the multiplicity of sets comprises at least two sets of nucleic acid primers selected from the sets according to any embodiment of the present disclosure. In some embodiments, the kit further comprises one or more additional isolated nucleic acid primers suitable for LAMP and detection of a multiplicity of bacterial genomes.

In some embodiments, the one or more additional isolated nucleic acid primers as embodied herein reduce the duration of time necessary to perform the LAMP and detection of a multiplicity of bacterial genomes. In some embodiments, the one or more additional isolated nucleic acid primers reduce the duration of time necessary to perform the LAMP and detection of a multiplicity of bacterial genomes by at least 5 minutes, at least 7 minutes, at least 10 minutes, at least 12 minutes, at least 15 minutes, at least 17 minutes, or at least 20 minutes.

In some embodiments, the multiplicity of sets of nucleic acid primers mediate amplification of one or more conserved regions of the bacterial genome, optionally wherein the one or more conserved regions comprise a 16S, 23S, and/or rpoB gene sequence.

In some embodiments, the multiplicity of bacterial genomes comprises genomes from two or more bacterial species. In some embodiments, the bacterial species are selected from the group consisting of: *Acinetobacter ursingii, Acinetobacter baumannii, Bacillus cereus, Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Haemophilus influenzae, Klebsiella aerogenes, Klebsiella oxytoca, Klebsiella pneumoniae, Lactobacillus rhamnosus, Listeria monocytogenes, Morganella morganii, Pantoea agglomerans, Pasteurella multocida, Proteus mirabilis, Pseudomonas aeruginosa, Pseudomonas putida, Raoultella ornithinolytica, Salmonella enterica, Serratia liquefaciens, Serratia marcescens, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans, Staphylococcus warneri, Stenotrophomonas maltophilia, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and/or *Streptococcus sanguinis.*

Aspects of the disclosure include a method of detecting a multiplicity of bacterial genomes using a kit according to any embodiment of the present disclosure.

Aspects of the disclosure include a primer set for detecting the order Lactobacillales, comprising an oligonucleotide set containing nucleic acid sequences represented by SEQ ID NOs: 1-4, the primer set being capable of amplifying a particular conserved region of a Lactobacillales gene sequence. In some embodiments, the primer set for detecting the order Lactobacillales further comprises one or more additional isolated nucleic acid sequences comprising SEQ ID NOs: 5 and/or 6. In some embodiments, the particular conserved region of a Lactobacillales gene sequence comprises a 16S, 23S, and/or rpoB gene sequence.

Aspects of the disclosure include a primer set for detecting the order *Staphylococcus*, comprising an oligonucleotide set containing nucleic acid sequences represented by SEQ ID NOs: 7-10, the primer set being capable of amplifying a particular conserved region of a *Staphylococcus* gene sequence. In some embodiments, the primer set for detecting the order *Staphylococcus* further comprises one or more additional isolated nucleic acid sequences comprising SEQ ID NOs: 11 and/or 12. In some embodiments, the particular conserved region of a *Staphylococcus* gene sequence comprises a 16S, 23S, and/or rpoB gene sequence.

Aspects of the disclosure include a primer set for detecting the genus *Acinetobacter*, comprising an oligonucleotide set containing nucleic acid sequences represented by SEQ ID NOs: 13-16, the primer set being capable of amplifying a particular conserved region of an *Acinetobacter* gene sequence. In some embodiments, the primer set for detecting the genus *Acinetobacter* further comprises one or more additional isolated nucleic acid sequences comprising SEQ ID NOs: 17 and/or 18. In some embodiments, the particular conserved region of an *Acinetobacter* gene sequence comprises a 16S, 23S, and/or rpoB gene sequence.

Aspects of the disclosure include a primer set for detecting the order Enterobacterales, comprising an oligonucleotide set containing nucleic acid sequences represented by SEQ ID NOs: 19-22, the primer set being capable of amplifying a particular conserved region of an Enterobacterales gene sequence. In some embodiments, the primer set for detecting the order Enterobacterales further comprises one or more additional isolated nucleic acid sequences comprising SEQ ID NOs: 23 and/or 24. In some embodiments, the particular conserved region of an Enterobacterales gene sequence comprises a 16S, 23S, and/or rpoB gene sequence.

Aspects of the disclosure include a primer set for detecting the order Pasteurellales, comprising an oligonucleotide set containing nucleic acid sequences represented by SEQ ID NOs: 25-28, the primer set being capable of amplifying a particular conserved region of a Pasteurellales gene sequence. In some embodiments, the primer set for detecting the order Pasteurellales further comprises one or more additional isolated nucleic acid sequences comprising SEQ ID NOs: 29 and/or 30. In some embodiments, the particular conserved region of a Pasteurellales gene sequence comprises a 16S, 23S, and/or rpoB gene sequence.

Aspects of the disclosure include a primer set for detecting the order Pseudomonadales, comprising an oligonucleotide set containing nucleic acid sequences represented by SEQ ID NOs: 31-34, the primer set being capable of amplifying a particular conserved region of a Pseudomonadales gene sequence. In some embodiments, the primer set for detecting the order Pseudomonadales further comprise one or more additional isolated nucleic acid sequences comprising SEQ ID NOs: 35 and/or 36. In some embodiments, the particular conserved region of a Pseudomonadales gene sequence comprises a 16S, 23S, and/or rpoB gene sequence.

These and other aspects and embodiments of the invention are illustrated and described below. Other compositions, methods, and features will be apparent to one with skill in the art upon examination of the following drawings and detailed description. It is intended that all such additional compositions and methods and features are within the scope of the present invention.

BRIEF DESCRIPTION OF THE FIGURES

The following drawings are illustrative of embodiments of the invention and are not meant to limit the scope of the invention as encompassed by the claims.

FIGS. 1A-1D encompass gram-negative bacteria (FIG. 1A: *Acinetobacter*; FIG. 1B: Enterobacterales; FIG. 1C: Pasteurellales; FIG. 1D: Pseudomonadales), and FIGS. 1E and 1F encompass gram-positive types (FIG. 1E: Lactobacillales; FIG. 1F: *Staphylococcus*).

FIGS. 2A-2C demonstrate the breadth of these primer sets, which also maintain specificity as shown with the representative non-target species. FIG. 2A shows representative species targeted in the Enterobacterales order. FIG. 2B shows representative species targeted in the Lactobacillales order. FIG. 2C shows representative species targeted in the *Staphylococcus* genus.

FIG. 3A shows that only Sample 2 shows a positive signal across all six primer sets and is positive for the *Staphylococcus* primer set. FIG. 3B shows sequencing data confirming that Sample 2 contains significant amounts of bacterial genomes, which are identified as *Staphylococcus lugdunensis*.

FIG. 5A shows results from a first clinical sample, which tested positive for Pseudomonadales across all four subsamples. FIG. 5B shows results from a second clinical sample, which did not test positive for any of the target bacteria. FIG. 5C shows results from a third clinical sample, which tested positive for both Lactobacillales and *Staphylococcus* across all four subsamples, respectively.

FIG. 6A shows the detection of Pseudomonadales in all four subsamples of the first clinical sample, as indicated by a positive signal observed prior to the predetermined time threshold (dotted line). FIG. 6B shows that *Staphylococcus* was not detected in any subsample of the first clinical sample, as indicated by the lack of positive signal prior to the predetermined time threshold (dotted line).

FIG. 7A shows that Pseudomonadales was not detected in any subsample of the second clinical sample, as indicated by the lack of positive signal prior to the predetermined time threshold (dotted line). FIG. 7B shows that *Staphylococcus* was not detected in any subsample of the second clinical sample, as indicated by the lack of positive signal prior to the predetermined time threshold (dotted line).

FIG. 8A shows that Pseudomonadales was not detected in any subsample of the third clinical sample, as indicated by the lack of positive signal prior to the predetermined time threshold (dotted line). FIG. 8B shows the detection of *Staphylococcus* in all four subsamples of the third clinical sample, as indicated by a positive signal observed prior to the predetermined time threshold (dotted line).

FIG. 9A shows that the top pathogen species present in the first clinical sample was *Pseudomonas aeruginosa*, with quantities ranging from 17.79 to 363.75 Mb measured in each subsample. FIG. 9B shows that the top pathogen species present in the second clinical sample was Torque teno midi virus (a non-bacterial pathogen), with quantities ranging from 0.02 to 1.69 Mb measured in each subsample. FIG. 9C shows that the top pathogen species present in the third clinical sample was *Staphylococcus aureus*, with quantities ranging from 109.34 to 494.74 Mb measured in each subsample.

DETAILED DESCRIPTION

Figure 1A:
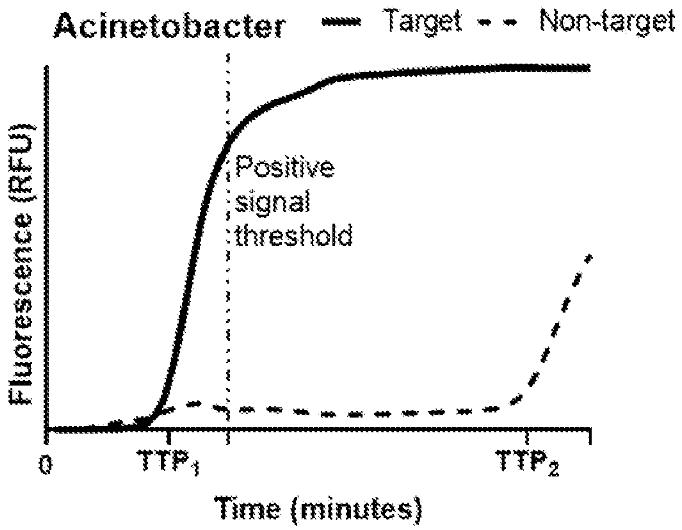
FIGS. 1A-1F show representative target and non-target genomes across the six primer sets described herein. For each primer set depicted in FIGS. 1A-1F, the dotted line represents the established threshold to determine a positive signal, which indicates the presence of bacteria. Positive target signals, where the time-to-positive ($TTP_1$, noted on the x-axis) is earlier than the established cutoffs, are shown in black, solid lines. Non-target signals, where $TTP_2$ (if relevant) amplifies after the established cutoff, are shown in black, dashed lines.
Figure 1B:
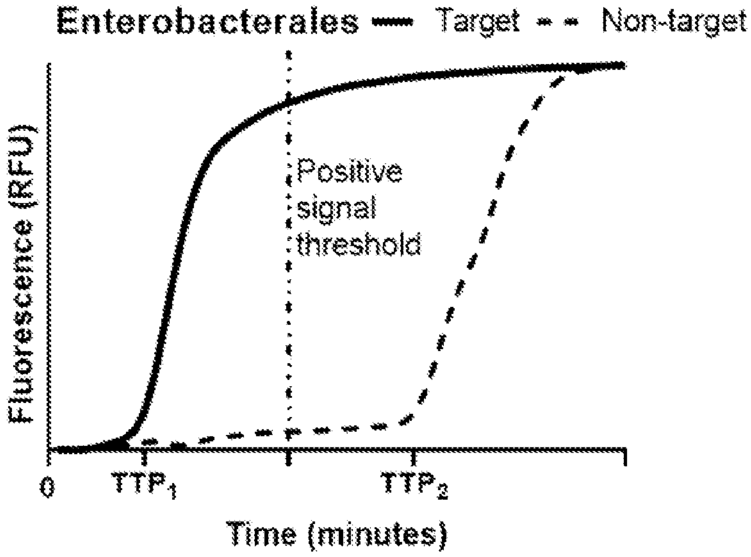
Figure 1C:
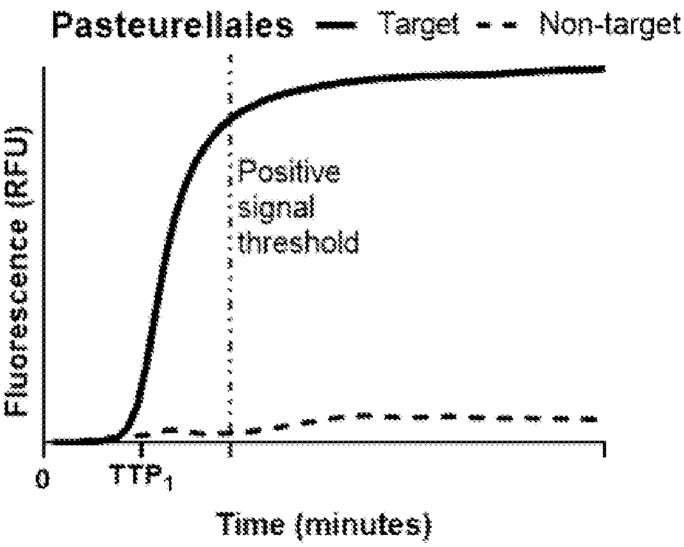
Figure 1D:
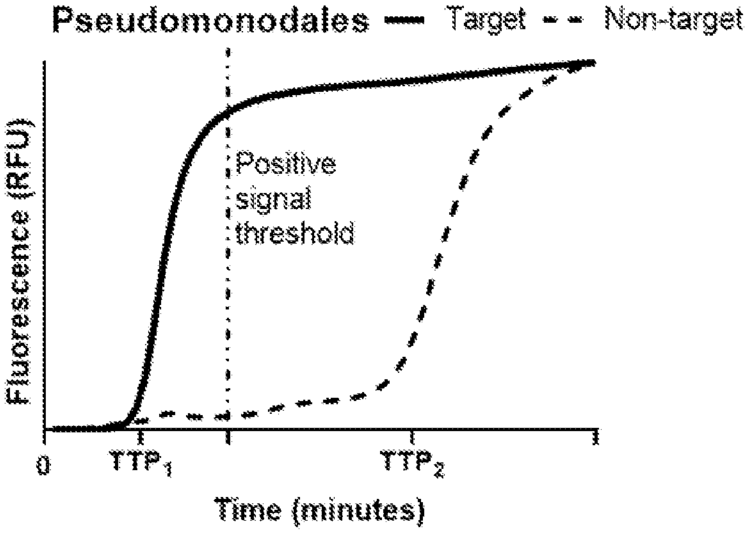

The present disclosure relates to methods, compositions (e.g., primers, primer sets, and multiplicities of primer sets), and kits useful for detecting a multiplicity of bacterial genomes present in a sample (e.g., a biological sample obtained from a subject exhibiting one or more signs or symptoms of bacteremia). Specifically, the present disclosure relates to nucleic acid primers, primer sets, and multiplicities of primer sets that allow for broad (e.g., species non-specific) detection of bacterial genomes present in such a sample using loop-mediated isothermal amplification (LAMP).

Principles of the Invention

The present invention can be embodied in different forms and should not be construed as limited to the embodiments set forth herein. Rather, these embodiments are merely illustrative of certain preferred or exemplary embodiments. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Bacteremia is currently the leading cause of in-hospital deaths in the United States, yet the standard, culture-based diagnostic methods can require several days to identify bacterial species within a sample from a subject, and often include false negatives. Certain molecular-based diagnostics (e.g., polymerase-based assays) leverage polymerase chain reaction (PCR) and its derivatives to address the issues of low sensitivity and slow turnaround time. While such methods are appropriate for assays with only one or two targets, utilizing these methods for a breadth of targets (e.g., a multiplicity of bacterial genomes) is often challenging, due to difficulties with cross reactivity and off-target amplification. Therefore, a new approach is needed that leverages the high sensitivity and speed of molecular-based methods while broadly detecting pathogenic bacteria, without compromising sensitivity and specificity. The present invention provides methods, compositions, and kits useful for screening samples across a wide breadth of bacteria (e.g., causative bacterial agents in bloodstream infections) with high confidence of determining true negative samples. These methods, compositions, and kits employ a set of loop-mediated isothermal amplification (LAMP) primers capable of detecting genomes belonging to more than fifty-two bacterial species that can be used either as a standalone platform or alongside blood culture, diagnostic tests, and sample preparation systems to determine the presence or absence of bacteria in blood.

Thus, in one aspect, the invention provides a multiplicity of sets of isolated nucleic acid primers suitable for LAMP and detection of a multiplicity of bacterial genomes. In some aspects, the present invention provides kits comprising isolated nucleic acid primers, sets of isolated nucleic acid primers, or a multiplicity of sets of isolated nucleic acid primers suitable for LAMP and detection of a multiplicity of bacterial genomes. Some aspects further contemplate methods of detecting a multiplicity of bacterial genomes using the kits comprising a multiplicity of sets.

Other aspects of the invention provide methods for detecting a multiplicity of bacterial genomes, the methods comprising: (a) providing a reaction mixture comprising at least one set of isolated nucleic acid primers, dNTPs, a DNA polymerase, and a DNA sample to be tested for the presence of bacterial nucleic acids; (b) incubating the reaction mixture under DNA polymerase reactions conditions to produce a reaction product comprising amplified bacterial nucleic acids; and (c) detecting the reaction product. In some embodiments, the method further comprises a second reaction mixture comprising at least one set of isolated nucleic acid primers, dNTPs, a DNA polymerase, and a DNA sample to be tested for the presence of bacterial nucleic acids, wherein the at least one set of the first reaction mixture differs from the at least one set of the second reaction mixture.

In some embodiments of any of the foregoing aspects, the multiplicity of sets of primers comprises at least two sets selected from the group consisting of: a set of four nucleic acid primers for detection of Lactobacillales comprising SEQ ID NOs: 1-4; a set of four nucleic acid primers for detection of *Staphylococcus* comprising SEQ ID NOs: 7-10; a set of four nucleic acid primers for detection of *Acinetobacter* comprising SEQ ID NOs: 13-16; a set of four nucleic acid primers for detection of Enterobacterales comprising SEQ ID NOs: 19-22; a set of four nucleic acid primers for detection of Pasteurellales comprising SEQ ID NOs: 25-28; and a set of four nucleic acid primers for detection of Pseudomonadales comprising SEQ ID NOs: 31-34. In some embodiments, the multiplicity of sets of primers further comprises one or more additional isolated nucleic acid primers suitable for LAMP and detection of a multiplicity of bacterial genomes. In some embodiments, the one or more additional isolated nucleic acid primers comprise one or more of SEQ ID NOs: 5, 6, 11, 12, 17, 18, 23, 24, 29, 30, 35, and/or 36.

Definitions

All scientific and technical terms used herein, unless otherwise defined below, are intended to have the same meaning as commonly understood by one of ordinary skill in the art to which this invention belongs. In the case of any conflict, the present specification, including definitions, will control. References to techniques employed herein are intended to refer to the techniques as commonly understood in the art, including variations on those techniques or substitutions of equivalent or later-developed techniques which would be apparent to one of skill in the art. In order to more clearly and concisely describe the subject matter which is the invention, the following definitions are provided for certain terms which are used in the specification and appended claims.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable that is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

As used herein, "amplification" refers to the process of increasing the number of copies of a specific nucleotide sequence in a population of nucleic acids by template-dependent and polymerase-dependent chemical synthesis. Methods of amplification include, but are not limited to, loop-mediated isothermal amplification (LAMP), polymerase chain reaction (PCR), strand displacement amplification (SDA), recombinase polymerase amplification (RPA), helicase dependent amplification (HDA), or transcription mediated amplification (TMA). In some embodiments, nucleic acid amplification is isothermal strand-displacement amplification, PCR, qPCR, RT-PCR, LAMP, RT-LAMP, RPA, HDA, degenerate oligonucleotide PCR, or primer extension pre-amplification.

As used herein, "bacteria" are single-celled organisms of the kingdom Prokaryota. Of interest in the methods of the invention are human pathogenic bacteria species. In some embodiments, the bacteria are *Staphylococcus aureus, Staphylococcus epidermidis, Streptococcus agalactiae, Enterococcus faecalis, Enterococcus faecium, Escherichia coli, Klebsiella pneumoniae*, or any other species associated with bacteremia.

As used herein, "bacteremia" refers to the presence of bacteria in the blood. In some embodiments, the bacteria present in the blood are infectious bacteria that cause disease in a host. However, bacteremia can also include non-pathogenic bacteria.

As used herein, a "clinical sample" is a biological sample obtained from a subject. A clinical sample may be directly obtained from the subject (e.g., by collecting the sample from the subject), or may be received indirectly from another person or entity (e.g., a healthcare provider or reference laboratory). A step of "obtaining" can include obtaining directly or indirectly.

As used herein, "complementary" refers to the ability of a polynucleotide sequence to selectively bind to or anneal to another polynucleotide sequence. The nucleic acid primers of the present invention are complementary to sequences of one population of DNA (e.g., bacterial DNA) in a mixed sample.

As used herein, a "conserved region" of a genome (e.g., a bacterial genome) refers to a sequence of at least 300 nucleotides conserved across at least 2 species. The nucleotide sequence may be conserved in DNA or RNA molecules. In some embodiments, the primers and primer sets described herein are designed to target specific sequences within a conserved region of a genome of interest. In some embodiments, the primers and primer sets described herein target a sequence that is at least 70% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%) identical to a specific sequence within a conserved region of a genome of interest.

As used herein, "enrichment" refers to the increase in abundance of one population of DNA (e.g., bacterial DNA) relative to the abundance of a second population (e.g., human DNA) in a mixed sample comprising at least two populations of DNA.

As used herein, "host DNA" refers to DNA derived from a human (e.g., a patient or subject), and "non-host DNA" refers to DNA derived from a bacterium.

As used herein, the term "mammal" refers to a warm-blooded vertebrate that is distinguished by the possession of hair or fur, the secretion of milk by females to nourish the young, and the birth of live young.

As used herein, a "mixed sample" is a sample that comprises DNA from at least two sources. In some embodiments, the mixed sample comprises a first population and a second population of nucleic acids. In some embodiments the first population of nucleic acids is mammalian DNA (e.g., human DNA) and the second population of nucleic acids is bacterial DNA. In some embodiments, the first population of nucleic acids is host DNA (e.g., patient DNA) and the second population of nucleic acids is non-host DNA (e.g., bacterial DNA).

As used herein with respect to recombinant polynucleotides, the term "modification" means any insertion, deletion, or substitution of a nucleotide in the recombinant sequence relative to a reference sequence (e.g., a naturally-occurring or a native sequence).

As used herein, "nucleic acid amplification" refers to a process for amplifying or multiplying a specific population or populations of nucleic acid molecules from a sample (e.g., clinical blood sample). In some embodiments, the population is from a pathogen, such as virus or bacterium. In some embodiments, the population is from the host of the sample (e.g., the clinical blood sample). The amount of nucleic acid molecules in the population can be expanded in any of several ways, including polymerase chain reaction (PCR), loop-mediated isothermal amplification (LAMP), strand displacement amplification (SDA), or transcription mediated amplification (TMA). In some embodiments, nucleic acid amplification is isothermal strand-displacement amplification, PCR, qPCR, RT-PCR, degenerate oligonucleotide PCR, LAMP, RT-LAMP, RPA, HDA, or primer extension pre-amplification.

As used herein, the term "oligonucleotide" is a polymer comprising nucleotide bases. The nucleotide bases can be composed of DNA nucleotides (e.g., A, C, G, T), RNA nucleotides (e.g., A, C, G, U), or mixtures of DNA nucleotides and RNA nucleotides. The nucleotide bases may be modified (e.g., pyDAD, puADA, 2'-O-methyl nucleotides, 2'-fluoro-deoxyribonucleotides, peptide nucleic acids (PNAs), locked nucleic acids (LNAs), morpholinos, bridged nucleotides (e.g., LNAs), or constrained ethyl nucleotides (cEts)).

As used herein with respect to nucleic acid sequences, the terms "percent identity," "sequence identity," "percentage similarity," "sequence similarity," and the like refer to a measure of the degree of similarity of two sequences based upon an alignment of the sequences that maximizes similarity between aligned nucleotides, and that is a function of the number of identical or similar nucleotides, the number of total residues or nucleotides, and the presence and length of gaps in the sequence alignment. A variety of algorithms and computer programs are available for determining sequence similarity using standard parameters. As used herein, sequence similarity is measured using the BLASTn program for nucleic acid sequences, which is available through the National Center for Biotechnology Information (www.ncbi.nlm.nih.gov/), and is described in, for example, Altschul, et al. (1990), *J. Mol. Biol.* 215:403-410; Gish and States (1993), *Nature Genet.* 3:266-272; Madden et al. (1996), *Meth. Enzymol.* 266:131-141; Altschul, et al. (1997), *Nucleic Acids Res.* 25:33 89-3402); Zhang, et al. (2000), *J. Comput. Biol.* 7(1-2):203-14. As used herein, percent similarity of two nucleic acid sequences (e.g., outer and loop primers; or inner primers) is the score based upon the following parameters for the BLASTn algorithm: word size=7; gap opening penalty=5; gap extension penalty=2; match reward=1; and mismatch penalty=−3; or word size=28; gap opening penalty=0; gap extension penalty=2.5; match reward=1; and mismatch penalty=−2.5.

As used herein, a "polymerase" refers to an enzyme which catalyzes the formation of a new nucleic acid molecule (e.g., DNA or RNA) utilizing an existing nucleic acid molecule (e.g., DNA or RNA) as a template to produce a complementary (or substantially complementary) polynucleotide sequence in the new molecule.

As used herein, a "primer" refers to a short, single-stranded DNA sequence used in polymerase-based amplification techniques, such as LAMP or PCR. An "isolated nucleic acid primer" is a primer comprising at least 15 nucleotides that does not take secondary structure into account, and which is suitable for use with LAMP.

As used herein, "species non-specific" means that no particular species is targeted or, in some embodiments, that no particular species is able to be targeted.

As used herein, "species non-specific amplification" refers to amplification of DNA (e.g., human or bacterial DNA) which uses primer sequences that are not limited to a single species but, rather, are characteristic of two or more species. Thus, the amplification is non-specific with respect to the multiple species of the DNA being amplified. For example, amplification methods using primers directed to 16S rRNA sequences that are conserved across many bacterial species can agnostically, or species non-specifically, enrich for multiple bacterial 16S rRNA sequences. Similarly, non-specific methods can amplify all or most sequences in a population of nucleic acids (e.g., using a mixture of random hexamer primers).

As used herein, "species non-specific bacterial DNA" refers to bacterial DNA having a sequence found in two or more bacterial species, but not found in human DNA.

As used herein, with respect to a nucleic acid, the term "recombinant" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a polynucleotide having a nucleic acid sequence identical to a naturally-occurring polynucleotide, but which is produced by cloning and expression in a heterologous host, is not considered recombinant.

INCORPORATION BY REFERENCE

The patent, scientific and technical literature referred to herein establish knowledge that was available to those skilled in the art at the time of filing. The entire disclosures of the issued U.S. patents, allowed applications, published and pending patent applications, and other references, including database citations for nucleic acid and protein sequences, that are cited herein are hereby incorporated by reference to the same extent as if each was specifically and individually indicated to be incorporated by reference.

Loop-Mediated Isothermal Amplification (LAMP)

The present invention employs loop-mediated amplification (LAMP), a DNA amplification technique developed by Notomi et al., (Notomi et al. (2000), *Nucleic Acids Research* 28:E63). Using LAMP, the target nucleic acid sequence is typically amplified at a constant temperature of 60-65° C. using either two pairs or three pairs of primers (e.g., 4 or 6 total primers) or 5 total primers, and a polymerase with high-strand displacement activity in addition to a replication activity. The LAMP reaction is a highly specific, sensitive, isothermal nucleic acid amplification reaction. LAMP employs a primer set of four essential primers, termed the forward inner primer (FIP), backward inner primer (BIP), forward displacement primer (F3) and backward displacement primer (B3). These four different primers are used to identify 6 distinct regions on the target sequence, which adds highly to the specificity of the method. Due to the specific nature of the action of these primers, the amount of DNA produced in LAMP is considerably higher than PCR-based amplification. The 4-primer LAMP method, using FIP, BIP, F3, and B3 primers, is the basic form of LAMP that was originally described for isothermal nucleic acid amplification. The system is composed of two loop-forming inner primers (FIP and BIP) and two outer primers (F3 and B3) whose primary function is to displace the DNA strands initiated from the inner primers thus allowing formation of the loops and strand displacement DNA synthesis.

Additionally, two optional primers can also be included (e.g., one or both optional primers can be included) which effectively accelerate the reaction; these are termed the forward loop primer (LF) and backward loop primer (LB). LF and LB bind to the loop sequences located between the F1/F1c and F2/F2c priming sites and the B1/B1c and B2/B2c priming sites. The addition of both loop primers significantly accelerates LAMP. In some embodiments, a 5-primer LAMP is used, wherein the 4 LAMP primers (F3. B3, FIP, and BIP) are used in conjunction with only one of the loop primers (either LF or LB). In some embodiments, a 6-primer LAMP is used, wherein the 4 LAMP primers (F3, B3. FIP, and BIP) are used in conjunction with both of the loop primers (LF and LB).

LAMP can be carried out using DNA or RNA (e.g., reverse transcriptase LAMP, or "RT-LAMP"). In some embodiments, LAMP amplifies target DNA, for example DNA conserved among a multiplicity of bacterial genomes. The inner primers (FIP and BIP) contain sequences of the sense and antisense strands of the target DNA, while the displacement primers (F3 and 133) and the loop primers (LF and LB) each contain a single target sequence. In total, seven target sequences are recognized when including one of the loop primers in the reaction (LF or LP), and eight target sequences are recognized when including both loop primers (LF and LB) in the reaction.

A DNA polymerase is used to amplify the target sequence of interest. Many different DNA polymerases may be used, the most common being the Bst DNA polymerase Large Fragment (e.g., Cat. No. M0275, New England BioLabs, Ipswich, MA), while the *Geobacillus* sp. large fragment (GspSSD) DNA polymerase (e.g., Cat. No. GSPSSD-001, OptiGene, West Sussex, United Kingdom) is used less often. Other exemplary polymerases include, but are not limited to, Vent (exo-) DNA polymerase (e.g., Cat. No. M0257, New England BioLabs, Ipswich, MA), Deep Vent DNA polymerase (e.g., Cat. No. M0258, New England BioLabs, Ipswich, MA), Deep Vent (exo-) DNA polymerase (e.g., Cat. No. M0259, New England BioLabs, Ipswich, MA), Klenow fragment (3'→5' exo-) (e.g., Cat. No. M0212, New England BioLabs, Ipswich, MA), Φ29 phage DNA polymerase (e.g., Cat. No. M0269, New England BioLabs, Ipswich, MA), Z-Taq™ DNA polymerase (e.g., Cat. No. R006B, TaKaRa Bio USA Inc., Mountain View, CA), and, KOD DNA polymerase (e.g., Cat. No. 71085-3, MilliporeSigma, St. Louis, MO). See, e.g., U.S. Pat. Nos. 5,814,506; 5,210,036; 5,500,363; 5,352,778; and U.S. Pat. No. 5,834,285; Nishioka, et al. (2001), *J. Biotechnol.* 88:141; Takagi, et al. (1997), *Appl. Environ. Microbiol.* 63:4504.

In some embodiments, RT-LAMP amplifies target RNA, for example RNA conserved among a multiplicity of bacterial genomes. In embodiments where the target nucleotide is RNA, any suitable reverse transcriptase may be employed. In embodiments where the target nucleotide is RNA, a thermophilic and/or thermostable reverse transcriptase is used. In some embodiments, the reverse transcriptase is thermostable. In some embodiments, the reverse transcriptase is thermophilic. Examples of reverse transcriptases used to convert an RNA target to DNA include, but are not limited to, Avian Myeloblastosis Virus (AMV) reverse transcriptase (e.g., Cat. No. M0277, New England BioLabs, Ipswich, MA), Moloney Murine Leukemia Virus (M-MuLV, MMLV, M-MLV) reverse transcriptase (e.g., Cat. No. M0253, New England BioLabs, Ipswich, MA), EpiScript Rnase H-reverse transcriptase (e.g., Cat. No. ERT12910, Lucigen, Inc., Middleton, WI), AffinityScript reverse transcriptase (e.g., Cat. No. 600105, Agilent, Santa Clara, CA), Accuscript reverse transcriptase (e.g., Cat. No. 600089, Agilent, Santa Clara. CA), and ImProm-II reverse transcriptase (e.g., Cat. No. A3800, Promega, Madison, WI). Any genetically altered forms or variants of the aforementioned reverse transcriptases are also contemplated herein.

The exponential amplification of the LAMP or RT-LAMP reaction is initiated by the inner primers (FIP and BIP) binding to their DNA target. This is followed by DNA synthesis primed by a displacement primer (F3 or B3) which releases a single-stranded DNA. This single-stranded DNA serves as template for DNA synthesis primed by the second inner and displacement primers that hybridize to the other end of the target. This produces a stem-loop DNA structure. In subsequent LAMP cycling, one inner primer hybridizes to the loop on the product and initiates displacement DNA synthesis. This yields the original stem-loop DNA and a new stem-loop DNA with a stem twice as long. The cycling reaction typically continues with accumulation of around $10^9$ copies of target in less than an hour. The inclusion of one or two loop primers (e.g., LF and/or LB) accelerates the LAMP reaction by hybridizing to the stem-loops, except for the loops that are hybridized by the inner primers, and prime strand displacement DNA synthesis.

A single-stranded loop portion can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides which can be detected, and which are considered the "target nucleic acid." By "portion" it is meant that the single-stranded nucleic acid of the loop may not wholly comprise the target nucleic acid, but may comprise the target nucleic acid as well as other nucleic acids. It can also mean that only a portion of the target nucleic acid is exposed in the single stranded portion of the loop product, while the remaining portion of the target nucleic acid is in the double-stranded portion of the loop product.

A variety of LAMP amplification detection methods exist. Non-specific target detection may be obtained through visual identification of a turbid sample as magnesium pyrophosphate precipitates in a positive LAMP reaction. For better visibility of a positive reaction, various agents, such as a pH indicator solution (e.g., Cat. No. M1800. New England BioLabs, Ipswich, MA), hydroxy naphthol blue, or calcein, may be added to the reaction. Alternatively, fluorescent detection may be achieved using a DNA intercalating dye, such as EvaGreen, SYTO-9, SYTO-82, SYBR green, Picogreen, or propidium iodide, which is added to the reaction reagent or added after the completion of the reaction for end point analysis.

Detecting the amplification of a specific target of interest by the LAMP reaction may also be achieved using various hybridization probe-based methods. For example, detection may be achieved by labelling a loop primer with a fluorophore and adding a complementary DNA probe labelled with a quencher molecule. By leveraging the Förster Resonance Energy Transfer (FRET) between the fluorophore and quencher, the bound loop primer and probe will not fluoresce in the absence of LAMP amplicons. Initially, the loop primer will bind the DNA probe, and the fluorophore will not emit light. As the LAMP reaction proceeds, binding of the loop primer to the LAMP amplicon is more favorable than binding to the probe; thus, the loop primer will disassociate from the probe, bind onto the amplicon, and emit fluorescence (see, e.g., Jiang, Y. S., et al., (2015), *Anal. Chem.,* 87(6): 3314-20). LAMP products may also readily be identified using gel electrophoresis which visualizes distinct banding patterns depending on the specific target and primers used. The technique is well-known to the skilled person and described in detail in, for example, Nagamine et al. (2002), *Molecular and Cellular Probes* 16:223-229.

LAMP can amplify nucleic acids from a wide variety of samples, including clinical samples as described elsewhere herein. These samples include, but are not limited to, bodily fluids (e.g., blood, urine, serum, lymph, saliva, sputum, joint fluid, cerebral spinal fluid, anal and vaginal secretions, perspiration, and semen of virtually any organism, for example mammals, such as humans): environmental samples (including, but not limited to, air, agricultural, water, and soil samples); plant materials; biological warfare agent samples; research samples (e.g., the sample may be the product of an amplification reaction, for example general amplification of genomic DNA (gDNA)); purified samples (e.g., purified gDNA, RNA, proteins, etc.); and raw samples (bacteria, virus, gDNA, etc.). As will be appreciated by those in the art, virtually any experimental manipulation may have been done on the sample. Some embodiments utilize siRNA, rRNA, and microRNA as target sequences. Some embodiments utilize nucleic acid samples from stored (e.g., frozen and/or archived) or fresh tissues.

Loop-Mediated Isothermal Amplification (LAMP) Primers

The present disclosure relates to nucleic acid primers, primer sets, and multiplicities of primer sets that allow for broad (e.g., species non-specific) detection of bacterial genomes present in such a sample using loop-mediated isothermal amplification (LAMP). In some embodiments, a multiplicity of primer sets comprises one or more isolated nucleic acid primer sets suitable for LAMP. In some embodiments, a multiplicity of primer sets comprises 1, 2, 3, 4, 5, 6, 7, 8, or more than 8 isolated nucleic acid primer sets suitable for LAMP. In some embodiments, a multiplicity of primer sets comprises 6 isolated nucleic acid primer sets suitable for LAMP. By "suitable for LAMP" it is meant that the primers, primer sets, and multiplicities of primer sets disclosed herein are compatible with and can be used for LAMP and LAMP-related techniques (e.g., RT-LAMP).

In some embodiments, a primer suitable for LAMP comprises an isolated nucleic acid primer. In some embodiments, an isolated nucleic acid primer comprises at least 15 nucleotides. In some embodiments, an isolated nucleic acid primer comprises at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides, at least 31 nucleotides, at least 32 nucleotides, at least 33 nucleotides, at least 34 nucleotides, at least 35 nucleotides, at least 36 nucleotides, at least 37 nucleotides, at least 38 nucleotides, at least 39 nucleotides, at least 40 nucleotides, at least 41 nucleotides, at least 42 nucleotides, at least 43 nucleotides, at least 44 nucleotides, at least 45 nucleotides, at least 46 nucleotides, at least 47 nucleotides, at least 48 nucleotides, at least 49 nucleotides, or at least 50 nucleotides. In some embodiments, an isolated nucleic acid primer comprises between 15 and 50 nucleotides. In some embodiments, an isolated nucleic acid primer comprises 50 nucleotides. In some embodiments, an isolated nucleic acid primer comprises between 20 and 50 nucleotides. In some embodiments, an isolated nucleic acid primer comprises between 15 and 35 nucleotides. In some embodiments, an isolated nucleic acid primer comprises between 15 and 25 nucleotides.

In some embodiments, an isolated nucleic acid primer comprises any one of SEQ ID NOs: 1-36. In some embodiments, an isolated nucleic acid primer comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98% identity to SEQ ID NOs: 1-36, respectively. In some embodiments, an isolated nucleic acid primer comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98% identity to SEQ ID NOs: 1-36, respectively, and does not have any consecutive nucleotide substitutions. In some embodiments, an isolated nucleic acid primer comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98% identity to SEQ ID NOs: 1-36, respectively, and does not have nucleotide substitutions within the last 5, 6, or 7 nucleotides of the 3' end of the nucleotide sequence.

In some embodiments, a primer set suitable for LAMP comprises one or more isolated nucleic acid primers (e.g., one or more primers suitable for LAMP). In some embodiments, a primer set suitable for LAMP comprises 1, 2, 3, 4, 5, or 6 isolated nucleic acid primers. In some embodiments, a primer set suitable for LAMP comprises 4 isolated nucleic acid primers. In some embodiments, a primer set suitable for LAMP comprising 4 isolated nucleic acid primers further comprises one or more additional isolated nucleic acid primers suitable for LAMP and detection of a multiplicity of bacterial genomes. In some embodiments, a primer set suitable for LAMP comprises 5 isolated nucleic acid primers. In some embodiments, a primer set suitable for LAMP comprises 6 isolated nucleic acid primers.

In some embodiments, the one or more isolated nucleic acid primers comprise one or more of SEQ ID NOs: 1-4, 7-10, 13-16, 19-22, 25-28, and/or 31-34. In some embodiments, the one or more isolated nucleic acid primers comprise nucleotide sequences having at least 70% identity to any one or more of SEQ ID NOs: 1-4, 7-10, 13-16, 19-22, 25-28, and/or 31-34. In some embodiments, the one or more isolated nucleic acid primers comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to any one or more of SEQ ID NOs: 1-4, 7-10, 13-16, 19-22, 25-28, and/or 31-34, or any percentage contained therein.

In some embodiments, the one or more additional isolated nucleic acid primers comprise one or more of SEQ ID NOs: 5, 6, 11, 12, 17, 18, 23, 24, 29, 30, 35, and/or 36. In some embodiments, the one or more additional isolated nucleic acid primers comprise nucleotide sequences having at least 70% identity to any one or more of SEQ ID NOs: 5, 6, 11, 12, 17, 18, 23, 24, 29, 30, 35, and/or 36. In some embodiments, the one or more additional isolated nucleic acid primers comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to any one or more of SEQ ID NOs: 5, 6, 11, 12, 17, 18, 23, 24, 29, 30, 35, and/or 36, or any percentage contained therein.

In some embodiments, a primer set suitable for LAMP comprises one or more isolated nucleic acid primers able to detect one or more conserved regions of the bacterial genome (e.g., able to detect one or more regions of nucleic acids that are conserved across a multiplicity of bacterial species and/or families). In some embodiments, the one or more isolated nucleic acid primers target the 16S rRNA gene sequence. The 16s rRNA gene is present in all bacteria and consists of highly conserved nucleotide sequences, interspersed with variable regions that are genus- or species-specific (see, e.g., Zhou, L. and Zhang, J., (2010), *Acta Microbiologica Sinica,* 50(1): 7-14). In some embodiments, the one or more isolated nucleic acid primers target the 23S rRNA gene sequence. The 23S rRNA gene sequence is a 2904 nucleotide long (in *E. coli*) component of the large subunit (50S) of the bacterial/Archaean ribosome. The ribosomal peptidyl transferase activity resides in domain V of this rRNA, and this domain is the most common binding site for antibiotics that inhibit translation (see, e.g., Ludwig, W. and Schleifer, K. H., (1994), *FEMS Microbiology Reviews,* 15(2-3):155-73). In some embodiments, the one or more isolated nucleic acid primers target the rpoB gene sequence. The rpoB gene encodes the β subunit of bacterial RNA polymerase (see, e.g., Adékambi, T., et al., (2009), *Cell,* 17(1): 37-45). It will be understood that other genes are known in the art to be well conserved, and may include sequences that are similar to transfer RNA, operons, DNA polymerases, and sequences that encode for nucleotide-binding domains of ATP-binding cassette transporters. Examples of such other well-conserved genes can be found, for example, in Isenbarger, T. A., et al., (2008), *Origins of Life and Evolution of Biospheres,* 38(6): 517-33 and Siefert, J. L., et al., (1997), *J. Mol. Evol.,* 45(5): 467-72.

Lactobacillales

In some embodiments, a primer set suitable for LAMP comprises one or more isolated nucleic acid primers able to detect bacterial genomes (e.g., one or more bacterial species) taxonomically classified in the order Lactobacillales. In some embodiments, the primer set suitable for LAMP comprises four nucleic acid primers for detection of Lactobacillales. In some embodiments, the four nucleic acid primers for detection of Lactobacillales comprise a forward inner primer (FIP), backward inner primer (BIP), forward displacement primer (F3) and backward displacement primer (B3). In some embodiments, the four nucleic acid primers (e.g., the FIP, BIP, F3, and B3) for detection of Lactobacillales comprise SEQ ID NOs: 1-4. In some embodiments, the four nucleic acid primers for detection of Lactobacillales comprise nucleotide sequences having at least 70% identity to SEQ ID NOs: 1-4. In some embodiments, the four nucleic acid primers for detection of Lactobacillales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-4, or any percentage contained therein.

In some embodiments, the primer set suitable for LAMP comprises five nucleic acid primers for detection of Lactobacillales. In some embodiments, the five nucleic acid primers for detection of Lactobacillales comprise an FIP, BIP, F3, B3, and forward loop primer (LF). In some embodiments, the five nucleic acid primers (e.g., the FIP, BIP, F3, B3, and LF) for detection of Lactobacillales comprise SEQ ID NOs: 1-5. In some embodiments, the five nucleic acid primers for detection of Lactobacillales comprise nucleotide sequences having at least 70% identity to SEQ ID NOs: 1-5. In some embodiments, the five nucleic acid primers for detection of Lactobacillales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-5, or any percentage contained therein.

In some embodiments, the five nucleic acid primers for detection of Lactobacillales comprise an FIP, BIP, F3, B3, and backward loop primer (LB). In some embodiments, the five nucleic acid primers (e.g., FIP, BIP, F3, B3, and LB) for detection of Lactobacillales comprise SEQ ID NOs: 1-4 and 6. In some embodiments, the five nucleic acid primers for detection of Lactobacillales comprise nucleotide sequences having at least 70% identity to SEQ ID NOs: 1-4 and 6. In some embodiments, the five nucleic acid primers for detection of Lactobacillales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-4 and 6, or any percentage contained therein.

In some embodiments, the primer set suitable for LAMP comprises six nucleic acid primers for detection of Lactobacillales. In some embodiments, the six nucleic acid primers for detection of Lactobacillales comprise an FIP, BIP, F3, B3, LF, and LB. In some embodiments, the six nucleic acid primers (e.g., FIP, BIP, F3, B3, LF, and LB) for detection of Lactobacillales comprise SEQ ID NOs: 1-6. In some embodiments, the six nucleic acid primers for detection of Lactobacillales comprise nucleotide sequences having at least 70% identity to SEQ ID NOs: 1-6. In some embodiments, the six nucleic acid primers for detection of Lactobacillales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-6, or any percentage contained therein.

*Staphylococcus*

In some embodiments, a primer set suitable for LAMP comprises one or more isolated nucleic acid primers able to detect bacterial genomes (e.g., one or more bacterial species) taxonomically classified in the genus *Staphylococcus*. In some embodiments, the primer set suitable for LAMP comprises four nucleic acid primers for detection of *Staphylococcus*. In some embodiments, the four nucleic acid primers for detection of *Staphylococcus* comprise a forward inner primer (FIP), backward inner primer (BIP), forward displacement primer (F3) and backward displacement primer (B3). In some embodiments, the four nucleic acid primers (e.g., the FIP, BIP, F3, and B3) for detection of *Staphylococcus* comprise SEQ ID NOs: 7-10. In some embodiments, the four nucleic acid primers for detection of *Staphylococcus* comprise nucleotide sequences having at least 70% identity to SEQ ID NOs: 7-10. In some embodiments, the four nucleic acid primers for detection of *Staphylococcus* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-10, or any percentage contained therein.

In some embodiments, the primer set suitable for LAMP comprises five nucleic acid primers for detection of *Staphylococcus*. In some embodiments, the five nucleic acid primers for detection of *Staphylococcus* comprise an FIP, BIP, F3, B3, and forward loop primer (LF). In some embodiments, the five nucleic acid primers (e.g., the FIP, BIP, F3, B3, and LF) for detection of *Staphylococcus* comprise SEQ ID NOs: 7-11. In some embodiments, the five nucleic acid primers for detection of *Staphylococcus* comprise nucleotide sequences having at least 70% identity to SEQ ID NOs: 7-11. In some embodiments, the five nucleic acid primers for detection of *Staphylococcus* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-11, or any percentage contained therein.

In some embodiments, the five nucleic acid primers for detection of *Staphylococcus* comprise an FIP, BIP, F3, B3, and backward loop primer (LB). In some embodiments, the five nucleic acid primers (e.g., FIP, BIP, F3, B3, and LB) for detection of *Staphylococcus* comprise SEQ ID NOs: 7-10 and 12. In some embodiments, the five nucleic acid primers for detection of *Staphylococcus* comprise nucleotide sequences having at least 70% identity to SEQ ID NOs: 7-10 and 12. In some embodiments, the five nucleic acid primers for detection of *Staphylococcus* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-10 and 12, or any percentage contained therein.

In some embodiments, the primer set suitable for LAMP comprises six nucleic acid primers for detection of *Staphylococcus*. In some embodiments, the six nucleic acid primers for detection of *Staphylococcus* comprise an FIP, BIP, F3, B3, LF, and LB. In some embodiments, the six nucleic acid primers (e.g., FIP, BIP, F3, B3, LF, and LB) for detection of *Staphylococcus* comprise SEQ ID NOs: 7-12. In some embodiments, the six nucleic acid primers for detection of *Staphylococcus* comprise nucleotide sequences having at least 70% identity to SEQ ID NOs: 7-12. In some embodiments, the six nucleic acid primers for detection of *Staphylococcus* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-12, or any percentage contained therein.

*Acinetobacter*

In some embodiments, a primer set suitable for LAMP comprises one or more isolated nucleic acid primers able to detect bacterial genomes (e.g., one or more bacterial species) taxonomically classified in the genus *Acinetobacter*. In some embodiments, the primer set suitable for LAMP comprises four nucleic acid primers for detection of *Acinetobacter*. In some embodiments, the four nucleic acid primers for detection of *Acinetobacter* comprise a forward inner primer (FIP), backward inner primer (BIP), forward displacement primer (F3) and backward displacement primer (B3). In some embodiments, the four nucleic acid primers (e.g., the FIP, BIP, F3, and B3) for detection of *Acinetobacter* comprise SEQ ID NOs: 13-16. In some embodiments, the four nucleic acid primers for detection of *Acinetobacter* comprise nucleotide sequences having at least 70% identity to SEQ ID NOs: 13-16. In some embodiments, the four nucleic acid primers for detection of *Acinetobacter* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-16, or any percentage contained therein.

In some embodiments, the primer set suitable for LAMP comprises five nucleic acid primers for detection of *Acinetobacter*. In some embodiments, the five nucleic acid primers for detection of *Acinetobacter* comprise an FIP, BIP, F3, B3, and forward loop primer (LF). In some embodiments, the five nucleic acid primers (e.g., the FIP, BIP, F3, B3, and LF) for detection of *Acinetobacter* comprise SEQ ID NOs: 13-17. In some embodiments, the five nucleic acid primers for detection of *Acinetobacter* comprise nucleotide sequences having at least 70% identity to SEQ ID NOs: 13-17. In some embodiments, the five nucleic acid primers for detection of *Acinetobacter* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-17, or any percentage contained therein.

In some embodiments, the five nucleic acid primers for detection of *Acinetobacter* comprise an FIP, BIP, F3, B3, and backward loop primer (LB). In some embodiments, the five nucleic acid primers (e.g., FIP, BIP, F3, B3, and LB) for detection of *Acinetobacter* comprise SEQ ID NOs: 13-16 and 18. In some embodiments, the five nucleic acid primers for detection of *Acinetobacter* comprise nucleotide sequences having at least 70% identity to SEQ ID NOs: 13-16 and 18. In some embodiments, the five nucleic acid primers for detection of *Acinetobacter* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-16 and 18, or any percentage contained therein.

In some embodiments, the primer set suitable for LAMP comprises six nucleic acid primers for detection of *Acinetobacter*. In some embodiments, the six nucleic acid primers for detection of *Acinetobacter* comprise an FIP, BIP, F3, B3, LF, and LB. In some embodiments, the six nucleic acid primers (e.g., FIP, BIP, F3, B3, LF, and LB) for detection of *Acinetobacter* comprise SEQ ID NOs: 13-18. In some embodiments, the six nucleic acid primers for detection of *Acinetobacter* comprise nucleotide sequences having at least 70% identity to SEQ ID NOs: 13-18. In some embodiments, the six nucleic acid primers for detection of *Acinetobacter* comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-18, or any percentage contained therein.

Enterobacterales

In some embodiments, a primer set suitable for LAMP comprises one or more isolated nucleic acid primers able to detect bacterial genomes (e.g., one or more bacterial species) taxonomically classified in the order Enterobacterales. In some embodiments, the primer set suitable for LAMP comprises four nucleic acid primers for detection of Enterobacterales. In some embodiments, the four nucleic acid primers for detection of Enterobacterales comprise a forward inner primer (FIP), backward inner primer (BIP), forward displacement primer (F3) and backward displacement primer (B3). In some embodiments, the four nucleic acid primers (e.g., the FIP, BIP, F3, and B3) for detection of Enterobacterales comprise SEQ ID NOs: 19-22. In some embodiments, the four nucleic acid primers for detection of Enterobacterales comprise nucleotide sequences having at least 70% identity to SEQ ID NOs: 19-22. In some embodiments, the four nucleic acid primers for detection of Enterobacterales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-22, or any percentage contained therein.

In some embodiments, the primer set suitable for LAMP comprises five nucleic acid primers for detection of Enterobacterales. In some embodiments, the five nucleic acid primers for detection of Enterobacterales comprise an FIP, BIP, F3, B3, and forward loop primer (LF). In some embodiments, the five nucleic acid primers (e.g., the FIP, BIP, F3, B3, and LF) for detection of Enterobacterales comprise SEQ ID NOs: 19-23. In some embodiments, the five nucleic acid primers for detection of Enterobacterales comprise nucleotide sequences having at least 70% identity to SEQ ID NOs: 19-23. In some embodiments, the five nucleic acid primers for detection of Enterobacterales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-23, or any percentage contained therein.

In some embodiments, the five nucleic acid primers for detection of Enterobacterales comprise an FIP, BIP, F3, B3, and backward loop primer (LB). In some embodiments, the five nucleic acid primers (e.g., FIP, BIP, F3, B3, and LB) for detection of Enterobacterales comprise SEQ ID NOs: 19-22 and 24. In some embodiments, the five nucleic acid primers for detection of Enterobacterales comprise nucleotide sequences having at least 70% identity to SEQ ID NOs: 19-22 and 24. In some embodiments, the five nucleic acid primers for detection of Enterobacterales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-22 and 24, or any percentage contained therein.

In some embodiments, the primer set suitable for LAMP comprises six nucleic acid primers for detection of Enterobacterales. In some embodiments, the six nucleic acid primers for detection of Enterobacterales comprise an FIP, BIP, F3, B3, LF, and LB. In some embodiments, the six nucleic acid primers (e.g., FIP, BIP, F3, B3, LF, and LB) for detection of Enterobacterales comprise SEQ ID NOs: 19-24. In some embodiments, the six nucleic acid primers for detection of Enterobacterales comprise nucleotide sequences having at least 70% identity to SEQ ID NOs: 19-24. In some embodiments, the six nucleic acid primers for detection of Enterobacterales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-24, or any percentage contained therein.

Pasteurellales

In some embodiments, a primer set suitable for LAMP comprises one or more isolated nucleic acid primers able to detect bacterial genomes (e.g., one or more bacterial species) taxonomically classified in the order Pasteurellales. In some embodiments, the primer set suitable for LAMP comprises four nucleic acid primers for detection of Pasteurellales. In some embodiments, the four nucleic acid primers for detection of Pasteurellales comprise a forward inner primer (FIP), backward inner primer (BIP), forward displacement primer (F3) and backward displacement primer (B3). In some embodiments, the four nucleic acid primers (e.g., the FIP, BIP, F3, and B3) for detection of Pasteurellales comprise SEQ ID NOs: 25-28. In some embodiments, the four nucleic acid primers for detection of Pasteurellales comprise nucleotide sequences having at least 70% identity to SEQ ID NOs: 25-28. In some embodiments, the four nucleic acid primers for detection of Pasteurellales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-28, or any percentage contained therein.

In some embodiments, the primer set suitable for LAMP comprises five nucleic acid primers for detection of Pasteurellales. In some embodiments, the five nucleic acid primers for detection of Pasteurellales comprise an FIP, BIP, F3, B3, and forward loop primer (LF). In some embodiments, the five nucleic acid primers (e.g., the FIP, BIP, F3, B3, and LF) for detection of Pasteurellales comprise SEQ ID NOs: 25-29. In some embodiments, the five nucleic acid primers for detection of Pasteurellales comprise nucleotide sequences having at least 70% identity to SEQ ID NOs: 25-29. In some embodiments, the five nucleic acid primers for detection of Pasteurellales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-29, or any percentage contained therein.

In some embodiments, the five nucleic acid primers for detection of Pasteurellales comprise an FIP, BIP, F3, B3, and backward loop primer (LB). In some embodiments, the five nucleic acid primers (e.g., FIP, BIP, F3, B3, and LB) for detection of Pasteurellales comprise SEQ ID NOs: 25-28 and 30. In some embodiments, the five nucleic acid primers for detection of Pasteurellales comprise nucleotide sequences having at least 70% identity to SEQ ID NOs: 25-28 and 30. In some embodiments, the five nucleic acid primers for detection of Pasteurellales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-28 and 30, or any percentage contained therein.

In some embodiments, the primer set suitable for LAMP comprises six nucleic acid primers for detection of Pasteurellales. In some embodiments, the six nucleic acid primers for detection of Pasteurellales comprise an FIP, BIP, F3, B3, LF, and LB. In some embodiments, the six nucleic acid primers (e.g., FIP, BIP, F3, B3, LF, and LB) for detection of Pasteurellales comprise SEQ ID NOs: 25-30. In some embodiments, the six nucleic acid primers for detection of Pasteurellales comprise nucleotide sequences having at least 70% identity to SEQ ID NOs: 25-30. In some embodiments, the six nucleic acid primers for detection of Pasteurellales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-30, or any percentage contained therein.

Pseudomonadales

In some embodiments, a primer set suitable for LAMP comprises one or more isolated nucleic acid primers able to detect bacterial genomes (e.g., one or more bacterial species) taxonomically classified in the order Pseudomonadales. In some embodiments, the primer set suitable for LAMP comprises four nucleic acid primers for detection of Pseudomonadales. In some embodiments, the four nucleic acid primers for detection of Pseudomonadales comprise a forward inner primer (FIP), backward inner primer (BIP), forward displacement primer (F3) and backward displacement primer (B3). In some embodiments, the four nucleic acid primers (e.g., the FIP, BIP, F3, and B3) for detection of Pseudomonadales comprise SEQ ID NOs: 31-34. In some embodiments, the four nucleic acid primers for detection of Pseudomonadales comprise nucleotide sequences having at least 70% identity to SEQ ID NOs: 31-34. In some embodiments, the four nucleic acid primers for detection of Pseudomonadales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-34, or any percentage contained therein.

In some embodiments, the primer set suitable for LAMP comprises five nucleic acid primers for detection of Pseudomonadales. In some embodiments, the five nucleic acid primers for detection of Pseudomonadales comprise an FIP, BIP, F3, B3, and forward loop primer (LF). In some embodiments, the five nucleic acid primers (e.g., the FIP, BIP, F3, B3, and LF) for detection of Pseudomonadales comprise SEQ ID NOs: 31-35. In some embodiments, the five nucleic acid primers for detection of Pseudomonadales comprise nucleotide sequences having at least 70% identity to SEQ ID NOs: 31-35. In some embodiments, the five nucleic acid primers for detection of Pseudomonadales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-35, or any percentage contained therein.

In some embodiments, the five nucleic acid primers for detection of Pseudomonadales comprise an FIP, BIP, F3, B3, and backward loop primer (LB). In some embodiments, the five nucleic acid primers (e.g., FIP, BIP, F3, B3, and LB) for detection of Pseudomonadales comprise SEQ ID NOs: 31-34 and 36. In some embodiments, the five nucleic acid primers for detection of Pseudomonadales comprise nucleotide sequences having at least 70% identity to SEQ ID NOs: 31-34 and 36. In some embodiments, the five nucleic acid primers for detection of Pseudomonadales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-34 and 36, or any percentage contained therein.

In some embodiments, the primer set suitable for LAMP comprises six nucleic acid primers for detection of Pseudomonadales. In some embodiments, the six nucleic acid primers for detection of Pseudomonadales comprise an FIP, BIP, F3, B3, LF, and LB. In some embodiments, the six nucleic acid primers (e.g., FIP, BIP, F3, B3, LF, and LB) for detection of Pseudomonadales comprise SEQ ID NOs: 31-36. In some embodiments, the six nucleic acid primers for detection of Pseudomonadales comprise nucleotide sequences having at least 70% identity to SEQ ID NOs: 31-36. In some embodiments, the six nucleic acid primers for detection of Pseudomonadales comprise nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-36, or any percentage contained therein.

Multiplicities of Sets

Aspects of the invention relate to multiplicities of primer sets that allow for broad (e.g., species non-specific) detection of bacterial genomes present in a sample using loop-mediated isothermal amplification (LAMP). In some embodiments, a multiplicity of primer sets comprises one or more isolated nucleic acid primer sets suitable for LAMP. In some embodiments, a multiplicity of primer sets comprises 1, 2, 3, 4, 5, 6, 7, 8, or more than 8 isolated nucleic acid primer sets suitable for LAMP. In some embodiments, a multiplicity of primer sets comprises 6 isolated nucleic acid primer sets suitable for LAMP.

In some embodiments, a multiplicity of sets comprises at least two sets selected from the group consisting of: a set of four nucleic acid primers for detection of Lactobacillales; a set of four nucleic acid primers for detection of *Staphylococcus*; a set of four nucleic acid primers for detection of *Acinetobacter*; a set of four nucleic acid primers for detection of Enterobacterales; a set of four nucleic acid primers for detection of Pasteurellales; and a set of four nucleic acid primers for detection of Pseudomonadales.

In some embodiments, a multiplicity of sets comprises at least two sets selected from the group consisting of: a set of four nucleic acid primers for detection of Lactobacillales comprising SEQ ID NOs: 1-4; a set of four nucleic acid primers for detection of *Staphylococcus* comprising SEQ ID NOs: 7-10; a set of four nucleic acid primers for detection of *Acinetobacter* comprising SEQ ID NOs: 13-16; a set of four nucleic acid primers for detection of Enterobacterales comprising SEQ ID NOs: 19-22; a set of four nucleic acid primers for detection of Pasteurellales comprising SEQ ID NOs: 25-28; and a set of four nucleic acid primers for detection of Pseudomonadales comprising SEQ ID NOs: 31-34.

In some embodiments, a multiplicity of sets comprises at least two sets selected from the group consisting of: a set of four nucleic acid primers for detection of Lactobacillales comprising nucleotide sequences having at least 70% identity to SEQ ID NOs: 1-4; a set of four nucleic acid primers for detection of *Staphylococcus* comprising nucleotide sequences having at least 70% identity to SEQ ID NOs: 7-10; a set of four nucleic acid primers for detection of *Acinetobacter* comprising nucleotide sequences having at least 70% identity to SEQ ID NOs: 13-16; a set of four nucleic acid primers for detection of Enterobacterales comprising nucleotide sequences having at least 70% identity to SEQ ID NOs: 19-22; a set of four nucleic acid primers for detection of Pasteurellales comprising nucleotide sequences having at least 70% identity to SEQ ID NOs: 25-28; and a set of four nucleic acid primers for detection of Pseudomonadales comprising nucleotide sequences having at least 70% identity to SEQ ID NOs: 31-34.

In some embodiments, a multiplicity of sets comprises at least two sets selected from the group consisting of: a set of four nucleic acid primers for detection of Lactobacillales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-4; a set of four nucleic acid primers for detection of *Staphylococcus* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-10; a set of four nucleic acid primers for detection of *Acinetobacter* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-16; a set of four nucleic acid primers for detection of Enterobacterales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-22; a set of four nucleic acid primers for detection of Pasteurellales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-28; and a set of four nucleic acid primers for detection of Pseudomonadales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-34.

In some embodiments, a multiplicity of sets comprises at least two sets selected from the group consisting of: a set of five nucleic acid primers for detection of Lactobacillales comprising SEQ ID NOs: 1-5; a set of five nucleic acid primers for detection of *Staphylococcus* comprising SEQ ID NOs: 7-11; a set of five nucleic acid primers for detection of *Acinetobacter* comprising SEQ ID NOs: 13-17; a set of five nucleic acid primers for detection of Enterobacterales comprising SEQ ID NOs: 19-23; a set of five nucleic acid primers for detection of Pasteurellales comprising SEQ ID NOs: 25-29; and a set of five nucleic acid primers for detection of Pseudomonadales comprising SEQ ID NOs: 31-35.

In some embodiments, a multiplicity of sets comprises at least two sets selected from the group consisting of: a set of five nucleic acid primers for detection of Lactobacillales comprising nucleotide sequences having at least 70% identity to SEQ ID NOs: 1-5; a set of five nucleic acid primers for detection of *Staphylococcus* comprising nucleotide sequences having at least 70% identity to SEQ ID NOs: 7-11; a set of five nucleic acid primers for detection of *Acinetobacter* comprising nucleotide sequences having at least 70% identity to SEQ ID NOs: 13-17; a set of five nucleic acid primers for detection of Enterobacterales comprising nucleotide sequences having at least 70% identity to SEQ ID NOs: 19-23; a set of five nucleic acid primers for detection of Pasteurellales comprising nucleotide sequences having at least 70% identity to SEQ ID NOs: 25-29; and a set of five nucleic acid primers for detection of Pseudomonadales comprising nucleotide sequences having at least 70% identity to SEQ ID NOs: 31-35.

In some embodiments, a multiplicity of sets comprises at least two sets selected from the group consisting of: a set of five nucleic acid primers for detection of Lactobacillales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-5; a set of five nucleic acid primers for detection of *Staphylococcus* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-11; a set of five nucleic acid primers for detection of *Acinetobacter* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-17; a set of five nucleic acid primers for detection of Enterobacterales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-23; a set of five nucleic acid primers for detection of Pasteurellales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-29; and a set of five nucleic acid primers for detection of Pseudomonadales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-35.

In some embodiments, a multiplicity of sets comprises at least two sets selected from the group consisting of: a set of five nucleic acid primers for detection of Lactobacillales comprising SEQ ID NOs: 1-4 and 6; a set of five nucleic acid primers for detection of *Staphylococcus* comprising SEQ ID NOs: 7-10 and 12; a set of five nucleic acid primers for detection of *Acinetobacter* comprising SEQ ID NOs: 13-16 and 18; a set of five nucleic acid primers for detection of Enterobacterales comprising SEQ ID NOs: 19-22 and 24; a set of five nucleic acid primers for detection of Pasteurellales comprising SEQ ID NOs: 25-28 and 30; and a set of five nucleic acid primers for detection of Pseudomonadales comprising SEQ ID NOs: 31-34 and 36.

In some embodiments, a multiplicity of sets comprises at least two sets selected from the group consisting of: a set of five nucleic acid primers for detection of Lactobacillales comprising nucleotide sequences having at least 70% identity to SEQ ID NOs: 1-4 and 6; a set of five nucleic acid primers for detection of *Staphylococcus* comprising nucleotide sequences having at least 70% identity to SEQ ID NOs: 7-10 and 12; a set of five nucleic acid primers for detection of *Acinetobacter* comprising nucleotide sequences having at least 70% identity to SEQ ID NOs: 13-16 and 18; a set of five nucleic acid primers for detection of Enterobacterales comprising nucleotide sequences having at least 70% identity to SEQ ID NOs: 19-22 and 24; a set of five nucleic acid primers for detection of Pasteurellales comprising nucleotide sequences having at least 70% identity to SEQ ID NOs: 25-28 and 30; and a set of five nucleic acid primers for detection of Pseudomonadales comprising nucleotide sequences having at least 70% identity to SEQ ID NOs: 31-34 and 36.

In some embodiments, a multiplicity of sets comprises at least two sets selected from the group consisting of: a set of five nucleic acid primers for detection of Lactobacillales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-4 and 6; a set of five nucleic acid primers for detection of *Staphylococcus* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-10 and 12; a set of five nucleic acid primers for detection of *Acinetobacter* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-16 and 18; a set of five nucleic acid primers for detection of Enterobacterales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-22 and 24; a set of five nucleic acid primers for detection of Pasteurellales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-28 and 30; and a set of five nucleic acid primers for detection of Pseudomonadales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-34 and 36.

In some embodiments, a multiplicity of sets comprises at least two sets selected from the group consisting of: a set of six nucleic acid primers for detection of Lactobacillales comprising SEQ ID NOs: 1-6; a set of six nucleic acid primers for detection of *Staphylococcus* comprising SEQ ID NOs: 7-12; a set of six nucleic acid primers for detection of *Acinetobacter* comprising SEQ ID NOs: 13-18; a set of six nucleic acid primers for detection of Enterobacterales comprising SEQ ID NOs: 19-24; a set of six nucleic acid primers for detection of Pasteurellales comprising SEQ ID NOs: 25-30; and a set of six nucleic acid primers for detection of Pseudomonadales comprising SEQ ID NOs: 31-36.

In some embodiments, a multiplicity of sets comprises at least two sets selected from the group consisting of: a set of six nucleic acid primers for detection of Lactobacillales comprising nucleotide sequences having at least 70% identity to SEQ ID NOs: 1-6; a set of six nucleic acid primers for detection of *Staphylococcus* comprising nucleotide sequences having at least 70% identity to SEQ ID NOs: 7-12; a set of six nucleic acid primers for detection of *Acinetobacter* comprising nucleotide sequences having at least 70% identity to SEQ ID NOs: 13-18; a set of six nucleic acid primers for detection of Enterobacterales comprising nucleotide sequences having at least 70% identity to SEQ ID NOs: 19-24; a set of six nucleic acid primers for detection of Pasteurellales comprising nucleotide sequences having at least 70% identity to SEQ ID NOs: 25-30; and a set of six nucleic acid primers for detection of Pseudomonadales comprising nucleotide sequences having at least 70% identity to SEQ ID NOs: 31-36.

In some embodiments, a multiplicity of sets comprises at least two sets selected from the group consisting of: a set of six nucleic acid primers for detection of Lactobacillales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 1-6; a set of six nucleic acid primers for detection of *Staphylococcus* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 7-12; a set of six nucleic acid primers for detection of *Acinetobacter* comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 13-18; a set of six nucleic acid primers for detection of Enterobacterales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 19-24; a set of six nucleic acid primers for detection of Pasteurellales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 25-30; and a set of six nucleic acid primers for detection of Pseudomonadales comprising nucleotide sequences having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% identity to SEQ ID NOs: 31-36.

Methods of Detection and Kits

Aspects of the present invention relate to kits comprising the primers, sets of primers, and multiplicities of primers as described herein, as well as methods of detecting bacterial genomes using such kits and multiplicities of primer sets.

Some embodiments therefore contemplate a kit comprising a multiplicity of sets of isolated nucleic acid primers suitable for loop-mediated isothermal amplification (LAMP) and detection of a multiplicity of bacterial genomes. In some embodiments, the multiplicity of sets comprises at least two sets selected from the group consisting of: a set of four nucleic acid primers for detection of Lactobacillales comprising SEQ ID NOs: 1-4; a set of four nucleic acid primers for detection of *Staphylococcus* comprising SEQ ID NOs: 7-10; a set of four nucleic acid primers for detection of *Acinetobacter* comprising SEQ ID NOs: 13-16; a set of four nucleic acid primers for detection of Enterobacterales comprising SEQ ID NOs: 19-22; a set of four nucleic acid primers for detection of Pasteurellales comprising SEQ ID NOs: 25-28; and a set of four nucleic acid primers for detection of Pseudomonadales comprising SEQ ID NOs: 31-34. In some embodiments, the multiplicity of sets further comprises one or more additional isolated nucleic acid primers suitable for LAMP and detection of a multiplicity of bacterial genomes. In some embodiments, the one or more additional isolated nucleic acid primers comprise one or more of SEQ ID NOs: 5, 6, 11, 12, 17, 18, 23, 24, 29, 30, 35, and/or 36. In some embodiments, the multiplicity of sets comprises any embodiment of primer, primer set, or multiplicity of primer sets as described in the present disclosure.

In some embodiments, each of the primers in a set are contained in separate containers within a kit. In some embodiments, each of the primer sets are contained in separate containers within a kit. In some embodiments, one or more of the primers in a set are contained in a single container within a kit. In some embodiments, one or more of the primer sets are contained in separate containers within a kit. In some embodiments, all of the primers in a set are contained in a single container within a kit. In some embodiments, all of the primer sets are contained in a single container within a kit.

Other embodiments contemplate a method for detecting a multiplicity of bacterial genomes, the method comprising: (a) providing a reaction mixture comprising at least one set of isolated nucleic acid primers, dNTPs, a DNA polymerase, and a DNA sample to be tested for the presence of bacterial nucleic acids; (b) incubating the reaction mixture under DNA polymerase reactions conditions to produce a reaction product comprising amplified bacterial nucleic acids; and (c) detecting the reaction product. In some embodiments, the method further comprises a second reaction mixture comprising at least one set of isolated nucleic acid primers, dNTPs, a DNA polymerase, and a DNA sample to be tested for the presence of bacterial nucleic acids, wherein the at least one set of the first reaction mixture differs from the at least one set of the second reaction mixture.

In some embodiments, the multiplicity of sets comprises any embodiment of primer, primer set, or multiplicity of primer sets as described in the present disclosure.

Pathogenic Bacteria

In some aspects, the present invention provides a multiplicity of sets of isolated nucleic acid primers suitable for loop-mediated isothermal amplification (LAMP) and detection of a multiplicity of bacterial genomes. In some embodiments, the bacterial genomes comprise one or more bacterial species. In some embodiments, the bacterial genomes comprise one or more bacterial species taxonomically classified in one or more of: the order Lactobacillales, the genus *Staphylococcus*, the genus *Acinetobacter*, the order Enterobacterales, the order Pasteurellales, and/or the order Pseudomonadales. Although some bacteria are normally present in healthy mammals, disruption of the normal balance between the bacteria and the human host, or the presence of abnormal or pathogenic bacteria within the host, can lead to infection.

Lactobacillales is a taxonomic order within the class Bacilli, which comprises lactic acid bacteria. The following families are contained within the order Lactobacillales, and are, in some embodiments, amplifiable and detectable using one or more of the nucleic acid primers of the present invention: Aerococcaceae, Carnobacteriaceae, Enterococcaceae, Lactobacillaceae, Leuconostocaceae, and Streptococcaceae. The following genera are contained with the order Lactobacillales, and are, in some embodiments, amplifiable and detectable using one or more of the nucleic acid primers of the present invention: *Abiotrophia, Aerococcus, Dolosicoccus, Eremococcus, Facklamia, Globicatella*, and *Ignavigranum* [all contained in the family Aerococcaceae]; *Agitococcus, Alkalibacterium, Allofustis, Alloiococcus, Atopobacter, Atopococcus, Atopostipes, Carnobacterium, Desemzia, Dolosigranulum, Granulicatella, Isobaculum, Jeotgalibaca, Lacticigenium, Marinilactibacillus, Pisciglobus*, and *Trichococcus* [all contained in the family Carnobacteriaceae]; *Bavariicoccus, Catellicoccus, Enterococcus, Melissococcus, Pilibacter, Tetragenococcus*, and *Vagococcus* [all contained in the family Enterococcaceae]; *Lactobacillus, Pediococcus*, and Sharpea [all contained in the family Lactobacillaceae]; *Convivina, Fructobacillus, Leuconostoc, Oenococcus*, and Weissella [all contained in the family Leuconostocaceae]; *Floricoccus, Lactococcus, Lactovum, Okadaella*, and *Streptococcus* [all contained in the family Streptococcaceae]; and *Aerosphaera, Carnococcus*, and *Chungangia* [all of uncertain placement, or the genera incertae sedis].

Enterobacterales, with its type genus *Enterobacter*, is a taxonomic order of Gram-negative bacteria within the class Gammaproteobacteria. The following families are contained within the order Enterobacterales, and are, in some embodiments, amplifiable and detectable using one or more of the nucleic acid primers of the present invention: Budviciaceae, Enterobacteriaceae, Erwiniaceae, Hafniaceae, Morganellaceae, Pectobacteriaceae, and Yersiniaceae. The following genera are contained within the order Enterobacterales, and are, in some embodiments, amplifiable and detectable using one or more of the nucleic acid primers of the present invention: *Aranicola, Arsenophonus, Averyella, Biostraticola, Brenneria, Buchnera, Budvicia, Buttiauxella, Cedecea, Chania, Citrobacter, Cosenzaea, Cronobacter, Dickeya, Edwardsiella, Enterobacillus, Enterobacter, Erwinia, Escherichia, Ewingella, Franconibacter, Gibbsiella, Grimontella, Guhaiyinggella, Hafnia, Izhakiella, Klebsiella, Kluyvera, Kosakonia, Leclercia, Lelliottia, Leminorella, Limnobaculum, Lonsdalea, Mangrovibacter, Margalefia, Metakosakonia, Mixta, Moellerella, Morganella, Obesumbacterium, Pantoea, Pectobacterium, Phaseolibacter, Photorhabdus, Phytobacter, Plesiomonas, Pluralibacter, Pragia, Proteus, Providencia, Pseudescherichia, Pseudocitrobacter, Rahnella, Raoultella, Rosenbergiella, Rouxiella, Saccharobacter, Salmonella, Samsonia, Scandinavium, Serratia, Shigella, Shimwellia, Siccibacter, Sodalis, Superficieibacter, Tatumella, Tiedjeia, Trabulsiella, Wigglesworthia, Xenorhabdus, Yersinia*, and *Yokenella.*

Pasteurellales is a taxonomic order within the class Gammaproteobacteria, and includes bacteria that live on mucosal surfaces of birds and mammals, especially in the upper respiratory tract. The following family is contained within the order Pasteurellales, and is, in some embodiments, amplifiable and detectable using one or more of the nucleic acid primers of the present invention: Pasteurellaceae. The following genera are contained within the order Pasteurellales, and are, in some embodiments, amplifiable and detectable using one or more of the nucleic acid primers of the present invention: *Actinobacillus, Aggregatibacter, Avibacterium, Basfia, Bibersteinia, Bisgaardia, Caviibacterium, Chelonobacter, Conservatibacter, Cricetibacter, Frederiksenia, Gallibacterium, Glaesserella, Haemophilus, Histophilus, Lonepinella, Mannheimia, Mesocricetibacter, Muribacter, Necropsobacter, Nicoletella, Otariodibacter, Pasteurella, Phocoenobacter, Rodentibacter, Seminibacterium, Terrahaemophilus, Testudinibacter, Ursidibacter, Vespertiliibacter*, and *Volucribacter.*

Pseudomonadales is a taxonomic order within the class Gammaproteobacteria. The following families are contained with the order Pseudomonadales, and are, in some embodiments, amplifiable and detectable using one or more of the nucleic acid primers of the present invention: Moraxellaceae, Pseudomonadaceae, and Ventosimonadaceae. The genus *Acinetobacter* is taxonomically classified as belonging to the order Pseudomonadales, and the family Moraxellaceae. The following genera are also contained with the order Pseudomonadales, and are, in some embodiments, amplifiable and detectable using one or more of the nucleic acid primers of the present invention: *Alkanindiges, Cavicella, Faucicola, Fluviicoccus, Moraxella, Paraperlucidibaca, Perlucidibaca*, and *Psychrobacter* [all from the family Moraxellaceae]; *Azomonas, Azorhizophilus, Azotobacter, Mesophilobacter, Oblitimonas, Permianibacter, Pseudomonas, Rugamonas*, and *Thiopseudomonas* [all from the family Pseudomonadaceae]; and *Ventosimonas* [from the family Ventosimonadaceae]. The following species are contained within the genus *Acinetobacter: A. albensis, A. apis, A. baumannii, A. baylyi, A. beijerinckii, A. bereziniae, A. bohemicus, A. boissieri, A. bouvetii, A. brisouii, A. calcoaceticus, A. celticus, A. colistiniresistens, A. courvalinii, A. defluvii, A. disperses, A. dijkshoorniae, A. equi, A. gandensis, A. gerneri, A. guangdongensis, A. guerrae, A. guillouiae, A. gyllenbergii, A. haemolyticus, A. harbinensis, A. indicus, A. junii, A. kookii, A. lactucae, A. larvae, A. lwoffii, A. modestus, A. nectaris, A. nosocomialis, A. parvus, A. pakistanensis, A. populi, A. portensis, A. proteolyticus, A. pittii, A. piscicola, A. pragensis, A. proteolyticus, A. puyangensis, A. qingfengensis, A. radioresistens, A. rudis, A. schindleri, A. seifertii, A. soli, A. tandoii, A. tjernbergiae, A. towneri, A. ursingii, A. variabilis, A. venetianus*, and *A. vivianii.*

The genus *Staphylococcus* is taxonomically classified is a genus of Gram-positive bacteria in the family Staphylococcaceae from the order Bacillales. The following species are contained within the genus *Staphylococcus*, and are, in some embodiments, amplifiable and detectable using one or more of the nucleic acid primers of the present invention: *S. argenteus, S. arlettae, S. agnetis, S. aureus, S. auricularis, S. caeli, S. capitis, S. caprae, S. carnosus, S. caseolyticus, S. chromogenes, S. cohnii, S. cornubiensis, S. condiment, S. debuckii, S. delphini, S. devriesei, S. edaphicus, S. epidermidis, S. equorum, S. felis, S. fleurettii, S. gallinarum, S. haemolyticus, S. hominis, S. hyicus, S. intermedius, S. jettensis, S. kloosii, S. leei, S. lentus, S. lugdunensis, S. lutrae, S. lyticans, S. massiliensis, S. microti, S. muscae, S. nepalensis, S. pasteuri, S. petrasii, S. pettenkoferi, S. piscifermentans, S. pseudintermedius, S. pseudolugdunensis, S. pulvereri, S. rostri, S. saccharolyticus, S. saprophyticus, S. schleiferi, S. schweitzeri, S. sciuri, S. simiae, S. simulans, S. stepanovicii, S. succinus, S. vitulinus, S. warneri*, and *S. xylosus.*

The methods, compositions, and kits of the present invention also contemplate the amplification and detection of certain bacterial genomes that are known in the art to be highly prevalent in cases of bacterial infection (e.g., bacteremia). In some embodiments, the certain bacterial genomes comprise certain bacterial species, which include *Staphylococcus aureus, Staphylococcus epidermidis, Streptococcus agalactiae, Enterococcus faecalis, Enterococcus faecium, Escherichia coli*, and/or *Klebsiella pneumoniae*, or any other bacterial species associated with clinical infection. In some embodiments, the bacterial genomes are associated with bacteremia.

*Staphylococcus aureus* (*S. aureus*) is a bacterium that is normally present in the human body and is frequently found in the nose, respiratory tract, and on the skin. Although *S. aureus* is not always pathogenic, it is a common cause of skin infections including abscesses, respiratory infections, and food poisoning. The common method of treating *S. aureus* infections is using antibiotics, although the emergence of antibiotic-resistant strains of *S. aureus* such as Methicillin-Resistant *S. aureus* (MRSA) and Vancomycin-Resistant *S. aureus* (VRSA) have become worldwide clinical health challenges.

*Staphylococcus epidermidis* (*S. epidermidis*) is a bacterium that is normally present in the human body, where it is frequently found on the skin. Although *S. epidermidis* is not generally pathogenic, subjects with compromised immune systems are at risk of developing *S. epidermidis* infections, and *S. epidermidis* poses a particular threat to subjects with surgical implants because it can grow on plastic surfaces and spread to the human body.

*S. epidermidis* strains are often resistant to antibiotics, including rifamycin, fluoroquinolones, gentamicin, tetracycline, clindamycin, and sulfonamides.

*Streptococcus agalactiae* (*S. agalactiae*) is a bacterium that is generally not pathogenic and can be found in the gastrointestinal and genitourinary tract in up to 30% of humans. Pathogenic infections due to *S. agalactiae* are of concern for neonates and immunocompromised individuals. *S. agalactiae* infections in adults can be life-threatening and include bacteremia, soft-tissue infections, osteomyelitis, endocarditis, and meningitis. *S. agalactiae* is increasingly resistant to clindamycin and erythromycin.

*Enterococcus faecalis* (*E. faecalis*) is a bacterium that inhabits the gastrointestinal tracts of humans and other mammals. However, *E. faecalis* can cause endocarditis, septicemia, urinary tract infections, and meningitis. *E. faecalis* infections can be life-threatening, particularly when the *E. faecalis* is resistant to treatment with gentamicin and vancomycin.

*Enterococcus faecium* (*E. faecium*) is a bacterium that inhabits the gastrointestinal tracts of humans and other mammals, but it may also be pathogenic, resulting in diseases such as meningitis and endocarditis. *E. faecium* infections can be life-threatening, particularly when the *E. faecium* is resistant to treatment with vancomycin.

*Escherichia coli* (*E. coli*) is a bacterium that inhabits the gastrointestinal tracts of humans and other mammals, but it may also be pathogenic, resulting in conditions such as gastroenteritis, urinary tract infections, neonatal meningitis, hemorrhagic colitis, and bacteremia. *E. coli* is increasingly resistant to multiple antibiotics, including fluoroquinolones, cephalosporins, and carbapenems.

*Klebsiella pneumoniae* (*K. pneumoniae*) is a bacterium that is normally found in the mouth, skin, and intestines of humans and other mammals. However, it can cause destructive changes to human and mammal lungs if inhaled, particularly to alveoli. *K. pneumoniae* infections are generally seen in subjects with a compromised immune system, including subjects with diabetes, alcoholism, cancer, liver disease, chronic obstructive pulmonary diseases, glucocorticoid therapy, and renal failure. *K. pneumoniae* is increasingly resistant to multiple antibiotics, including fluoroquinolones, cephalosporins, tetracycline, chloramphenicol, carbapenem, and trimethoprim/sulfamethoxazole.

In some embodiments, the one or more bacterial species able to be detected using the methods described herein are one or more of: *Acinetobacter ursingii, Acinetobacter baumannii, Bacillus cereus, Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Haemophilus influenzae, Klebsiella aerogenes, Klebsiella oxytoca, Klebsiella pneumoniae, Lactobacillus rhamnosus, Listeria monocytogenes, Morganella morganii, Pantoea agglomerans, Pasteurella multocida, Proteus mirabilis, Pseudomonas aeruginosa, Pseudomonas putida, Raoultella ornithinolytica, Salmonella enterica, Serratia liquefaciens, Serratia marcescens, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans, Staphylococcus warneri, Stenotrophomonas maltophilia, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and/or *Streptococcus sanguinis.*

Clinical Samples

In some embodiments, loop-mediated isothermal amplification (LAMP) and detection of a multiplicity of bacterial genomes is performed on a sample (e.g., a clinical sample). In some embodiments, samples (e.g., clinical samples) are obtained directly or indirectly from human subjects. In other embodiments, the samples (e.g., clinical samples) are obtained from non-human mammalian subjects. In some embodiments, the non-human mammalian subjects are companion animals such as dogs or cats; agricultural animals such as cows, pigs, sheep, goats or horses; or common laboratory animals such as rodents, rabbits, or non-human primates.

In some embodiments, the clinical sample is obtained or derived from blood, joint fluid, abscess fluid, sputum, urine, mucus, saliva, wound drainage, stool lymph, lavage, cerebral-spinal fluid (CSF), dialysis fluid, or any fluid aspirate or tissue extraction of human and/or other eukaryotic origin. In some embodiments, the clinical sample is obtained or derived from blood. In some embodiments, the clinical sample is obtained or derived from CSF. In some embodiments, the clinical sample is obtained or derived from joint fluid (e.g., prosthetic joint fluid). In some embodiments, the clinical sample is obtained or derived from tissue abscess fluid.

In some embodiments, the clinical sample comprises DNA (e.g., a total quantity of DNA) from between 1 and $10^8$ genomes (e.g., human, bacterial, and any other genomes) per milliliter. In some embodiments, the clinical sample comprises DNA from between 1 and 10 genomes per milliliter. In some embodiments, the clinical sample comprises DNA from between 1 and $10^2$ genomes per milliliter. In some embodiments, the clinical sample comprises DNA from between 1 and $10^3$ genomes per milliliter. In some embodiments, the clinical sample comprises DNA from between 1 and $10^4$ genomes per milliliter. In some embodiments, the clinical sample comprises DNA from between 1 and $10^5$ genomes per milliliter. In some embodiments, the clinical sample comprises DNA from between 1 and $10^6$ genomes per milliliter. In some embodiments, the clinical sample comprises DNA from between 1 and $10^7$ genomes per milliliter. In some embodiments, the clinical sample comprises DNA from between $10^3$ and $10^5$ genomes per milliliter. In some embodiments, the clinical sample comprises DNA from between $10^5$ and $10^6$ genomes per milliliter.

In some embodiments, the clinical sample comprises DNA (e.g., a total quantity of DNA) from between 0.1 and $10^4$ bacterial genomes per milliliter. In some embodiments, the clinical sample comprises DNA from between 0.1 and 10 bacterial genomes per milliliter. In some embodiments, the clinical sample comprises DNA from between 0.1 and $10^2$ bacterial genomes per milliliter. In some embodiments, the clinical sample comprises DNA from between 0.1 and $10^3$ bacterial genomes per milliliter. In some embodiments, the clinical sample comprises DNA from between $10^2$ and $10^3$ bacterial genomes per milliliter. In some embodiments, the clinical sample comprises DNA from between $10^3$ and $10^4$ bacterial genomes per milliliter.

In some embodiments, the subject has, or is suspected of having, a bacterial infection (e.g., bacteremia).

In some embodiments, the clinical sample is directly obtained by a person practicing the methods of the present invention. In some embodiments, the clinical sample is obtained indirectly by a person practicing the methods of the present invention. For example, in some embodiments, the clinical sample may be directly obtained from a subject by the subject or a physician, physician's assistant, nurse, laboratory technician or other healthcare personnel, and then may be indirectly obtained by a person practicing the methods of the present invention. As used herein, "obtaining" a clinical sample encompasses both directly and indirectly obtaining the sample according to the description herein.

Methods for obtaining clinical samples from a subject are known in the art, and may include, for example, identifying the patient prior to collecting a sample (e.g., by checking identification, armbands, etc.), labelling collection containers with appropriate patient identifiers in the presence of the patient, using at least two patient identifiers to label each container, sterilizing the collection site, drawing the samples into collection tubes in the proper sequence (e.g., blood culture tubes; coagulation tubes; serum tubes with or without clot activator, and with or without gel; heparin tubes, with or without gel plasma separator; EDTA tubes; oxalate and fluoride tubes; etc.), inverting the collection tubes end-to-end (i.e., gentle inversion) multiple times (e.g., 10 times) after collection, using proper collection containers, not transferring samples into secondary containers, delivering samples to the laboratory promptly after collection and/or processing the samples promptly after collection, avoiding hemolysis, drawing a first "flush" syringe prior to collecting the sample from a line, etc.

In some embodiments, a clinical sample comprises anywhere between 0.1 mL and 50 mL of sample material. In some embodiments, a clinical sample comprises 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 45, 40, 45, or 50, or any value included therein, such as 1.1, 1.2, 1.3, etc., mL of sample material. In some specific embodiments, a clinical sample comprises 16 mL of sample material.

Methods for handling and storing clinical samples are known in the art, and are described, for example, in Redrup et al. (2016), *AAPS J.* 18(2):290-93. In some embodiments, clinical samples are stored at room temperature (e.g., ~20-25° C.). In some embodiments, clinical samples are refrigerated (e.g., ~2-8° C., including 4° C.). In some embodiments, clinical samples are frozen (e.g., less than or equal to 0° C.).

In some embodiments, clinical samples are stored in sample containers. A variety of different sample containers are used in the art, and may be adapted to different types of clinical samples. For example, commonly used blood collection containers, blood culture bottles, plasma tubes, and blood culture media may include heparin, including lithium heparin and/or sodium heparin (e.g., Cat. Nos. 364960, 366667, 367871, 367878, 367884, 367886, 367960, 367961, 367962, and 367964 Vacutainer® collection tubes, BD Biosciences, Franklin Lakes, NJ), SPS (e.g., Cat. No. 364960 Vacutainer® collection tubes, Cat. Nos. 442022 and 442023, BACTECTM PLUS media, BD Biosciences, Franklin Lakes, NJ), ACD (Cat. Nos. 364816 and 364606 Vacutainer® collection tubes, BD Biosciences, Franklin Lakes, NJ), citrate (Cat. Nos. 363083 and 363080 Vacutainer® collection tubes, BD Biosciences, Franklin Lakes, NJ), sodium citrate (Cat. Nos. 369714 and 367947 Vacutainer® collection tubes, BD Biosciences, Franklin Lakes, NJ), or potassium EDTA (e.g., Cat. Nos. 367855, 367842, 367899, and 368589, Vacutainer® Plus Plastic K2EDTA Tubes, BD Biosciences, Franklin Lakes, NJ).

It will be appreciated that, in many cases, the most commonly used and commercially available sample containers are pre-loaded with preservatives and/or anticoagulants (e.g., sodium polyanetholesulfonate (SPS), heparin, lithium heparin, sodium heparin, citrate, sodium citrate, acid citrate dextrose (ACD), hyaluronate, dermatan sulfate polyanion, EDTA, potassium EDTA (K2EDTA), and chondroitin D-glucuronate anion) that may have the unintended effect of acting as nucleic acid amplification inhibitors during genetic identification or analysis of the various nucleic acids present in a sample (see, e.g., Fredericks and Relman (1998), *J. Clin. Microbiol.* 36(10): 2810-16; Qian et al. (2001), *J. Clin. Microbiol.* 39(10): 3578-85; and Regan et al. (2012), *J. Mol. Diagn.* 14(2): 120-29). In addition to such additives, blood components such as hemoglobin, lactoferrin, heme, and immunoglobulins can also interfere with nucleic acid amplification procedures. Such inhibition of and interference with amplification methods can be reduced without substantially harming the integrity or quality of the samples by adding proteinases (e.g., proteinase K) to the clinical blood samples, as described in International Patent Application No. PCT/US2020/020275, published on Sep. 3, 2020 under International Publication No. WO2020/176822, the entire disclosure of which is hereby incorporated by reference in its entirety.

Medical Conditions and Treatment

Methods, compositions (e.g., primers, sets of primers, and multiplicities of primers), and kits of the present invention can be used in the diagnosis and treatment of medical conditions, including infection by pathogenic bacteria. In some embodiments, methods, compositions (e.g., primers, sets of primers, and multiplicities of primers), and kits of the present invention are used to identify pathogenic bacteria causing an infection in a subject. In some embodiments, methods, compositions (e.g., primers, sets of primers, and multiplicities of primers), and kits of the present invention include and/or facilitate the amplification and detection of bacterial DNA in a mixed sample. In some embodiments, the mixed sample is a clinical sample from the subject. In some embodiments, the clinical sample is blood, prosthetic joint fluid, abscess fluid, sputum, blood, sputum, urine, mucus, saliva, wound drainage, stool, lymph, lavage, cerebral-spinal fluid, or any fluid aspirate or tissue extraction of human and/or other eukaryotic origin.

EXAMPLES

Example 1—Primers Suitable for LAMP

A consensus sequence was designed as the target template for six broad classes of bacteria: Lactobacillales, *Staphylococcus, Acinetobacter*, Enterobacterales, Pasteurellales, and Pseudomonadales. These bacteria were chosen based on bioinformatics data; the 16S rRNA gene was compared across targets of interest for regions of high conservation, and candidate bacteria were grouped based on gram-type and phylogeny. Regions of the 16S gene showing the highest conservation for the broadest number of bacteria were chosen, and the chosen conserved region(s) were used for primer design. Accordingly, using these consensus sequences, specific outer primers (F3 and B3), inner primers (FIP and BIP), and loop primers (LF and LB) were designed using the PrimerExplorerV5 software available on the Eiken Chemical Co. Ltd. Website.

The sequences of specific primer sets used here are shown in Table 1, below, and were synthesized by Integrated DNA Technologies, Ltd.

TABLE 1

Primers and primer sets.

| Assay | Name | Sequence (5' → 3') |
|---|---|---|
| *Lactobacillales* | F3 | GTGGGGAGCAAACAGGATT (SEQ ID NO: 1) |
| | B3 | TCTTCGCGTTGCTTCGAATT (SEQ ID NO: 2) |
| | FIP | TGCGTTAGCTGCGGCACTAAGGTCCACGCCGTAAACGATG (SEQ ID NO: 3) |
| | BIP | CCTGGGGAGTACGACCGCAACATGCTCCACCGCTTGTG (SEQ ID NO: 4) |
| | LF | CGGAAAGGGCCTAACACCTAGC (SEQ ID NO: 5) |
| | LB | GGTTGAAACTCAAAGGAATTGACG (SEQ ID NO: 6) |
| *Staphylococcus* | F3 | GCGCAGAGATATGGAGGAAC (SEQ ID NO: 7) |
| | B3 | AGGCGGAGTGCTTAATGC (SEQ ID NO: 8) |
| | FIP | TCCTGTTTGATCCCCACGCTTTGGCGAAGGCGACTTTCTG (SEQ ID NO: 9) |
| | BIP | AGATACCCTGGTAGTCCACGCCCACTAAGGGGCGGAAACC (SEQ ID NO: 10) |
| | LF | CGCACATCAGCGTCAGTTACAGA (SEQ ID NO: 11) |
| | LB | TAAACGATGAGTGCTAAGTGTTAGG (SEQ ID NO: 12) |
| *Acinetobacter* | F3 | ACCGCATACGTCCTACGG (SEQ ID NO: 13) |
| | B3 | GGTTCCCCCCATTGTCCA (SEQ ID NO: 14) |
| | FIP | GCCTTTACCCCACCAACTAGCTGAGAAAGCAGGGGATCTTCG (SEQ ID NO: 15) |
| | BIP | TGTAGCGGGTCTGAGAGGATGATATTCCCCACTGCTGCCTC (SEQ ID NO: 16) |
| | LF | GCTCATCTATTAGCGCAAGGTC (SEQ ID NO: 17) |
| | LB | AGACACGGCCCAGACTCCTA (SEQ ID NO: 18) |
| *Enterobacterales* | F3 | AGTCTTGTAGAGGGGGGTAG (SEQ ID NO: 19) |
| | B3 | CGTTAGCTCCGGAAGCCA (SEQ ID NO: 20) |
| | FIP | CAGTCTTTGTCCAGGGGGCCAATTCCAGGTGTAGCGGTGA (SEQ ID NO: 21) |
| | BIP | GCTCAGGTGCGAAAGCGTGGACCTCCAAGTCGACATCGTT (SEQ ID NO: 22) |
| | LF | CCACCGGTATTCCTCCAGATCTCTA (SEQ ID NO: 23) |
| | LB | TACCCTGGTAGTCCACGCCG (SEQ ID NO: 24) |
| *Pasteurellales* | F3 | TCCACGTGTAGCGGTGAA (SEQ ID NO: 25) |
| | B3 | TTATCACGTTAGCTTCGGGC (SEQ ID NO: 26) |
| | FIP | AGCGTCAGTACATTCCCAAGGGATGCGTAGAGATGTGGAGGA (SEQ ID NO: 27) |
| | BIP | GCGAAAGCGTGGGGAGCAAACCAATCCCCAAATCGACAGC (SEQ ID NO: 28) |
| | LF | GCTGCCTTCGCCTTCGGTA (SEQ ID NO: 29) |
| | LB | AGGATTAGATACCCTGGTAGTCCA (SEQ ID NO: 30) |

TABLE 1-continued

Primers and primer sets.

| Assay | Name | Sequence (5' → 3') |
|---|---|---|
| *Pseudomonadales* | F3 | GAAAGCAGGGGATCTTCGG (SEQ ID NO: 31) |
| | B3 | ACCTTCTTCACACACGCG (SEQ ID NO: 32) |
| | FIP | ACCAGTTACGGATCGTCGCCTTATCAGATGAGCCTAGGTCGG (SEQ ID NO: 33) |
| | BIP | CACACTGGAACTGAGACACGGTGGCTTTCGCCCATTGTCC (SEQ ID NO: 34) |
| | LF | GCCTTTACCCCACCAACTAGCTAAT (SEQ ID NO: 35) |
| | LB | ACTCCTACGGGAGGCAGCAG (SEQ ID NO: 36) |

Mastermixes were then prepared with the formulation shown in Table 2 for 20 μL reactions.

TABLE 2

Mastermix used for 20 μL reactions.

| 20× primer stock, prepared in 1× TE buffer: | Mastermix for all primer sets: |
|---|---|
| F3: 4 μM | 1× Isothermal Amplification Buffer (New England Biolabs) |
| B3: 4 μM | Magnesium sulfate: 2-6 mM (New England Biolabs) |
| FIP: 32 μM | dNTPs: 0.5-1.4 mM (New England Biolabs) |
| BIP: 32 μM | SYTO 82: 1 μM (Life Technologies, Inc.) |
| LF: 16 μM | 5% DMSO (Sigma Aldrich) |
| LB: 16 μM | 1× of 20× primer solution |
| | Bst 2.0 DNA polymerase: 0.4 U/μL (New England Biolabs) |

The 20 μL reaction was comprised of 3 μL of sample and 17 μL of the above mastermix (Table 2) per sample. Reactions were incubated at 64° C. for 30 minutes, and fluorescence readings were captured every 30 seconds. Fluorescent measurements require reading wavelengths with excitation between 400-600 nm and emission between 450-700 nm. The specific wavelength is dependent on the fluorophore for which the amplification mastermix is optimized. Following the 30 minute incubation, a heat-kill step was performed at 80° C. for 2 minutes to inactivate the polymerase and end the reaction. "No template" and positive controls were included with every run. No template controls consist of reactions where water or buffer is included, instead of the sample, to assess non-specific amplification that should arise from either contamination or dimerization of the primer sequences. Positive controls consist of reactions where genomic DNA of a representative bacterium encompassed by the primer set of known quantity (e.g., 1 ng) is included, instead of the sample.

The Figures exemplify the bacterial detection platform described herein, in conjunction with these Examples. For each primer set, there was an established cutoff by which to determine positive and negative signals; should a sample amplify before the established cutoff for a given primer set, the sample was considered positive. Signals were assessed using a metric called time to positive (TTP), which was calculated by curve fitting the amplification trace to a non-linear regression model, and then calculating the maximum value of the model's second derivative. The maximum value was then aligned with its related time point, and reported as the TTP. TTP is analogous to the inflection point prior the exponential phase of the trace, and is often used as a quantification metric across various amplification methods. Further information on calculating TTPs can be found, for example, in Sugawara, K., et al., (2012), *J. Gen. Plant Pathol.,* 78(6): 389-97 and Rutledge, R. G., (2004), *Nucl. Acid Res.,* 32(22): e178.

To validate the primer sets, bacteria of known ID and load were spiked into diluted blood samples. Samples were processed similarly to the sample processing method described in U.S. Pat. No. 10,544,446 to both remove human cells and decrease SPS carry over, which would inhibit downstream molecular amplification. In addition, detergents commonly used for selective lysis were coupled along with DNase I during sample treatment in order to further deplete human DNA similar to methods known in the literature (see, e.g., Charalampous, et al. (2019), *Nat. Biotechnol.* 37, 783-92; Street, et al. (2019), J. Clin. Microbio. 58(3); Hasan, et al. (2016), *J. Clin. Microbio.* 54(4); Shehadul Islam, et al. (2017), *Micromachines* 8(3): 83).

Figure 1E:
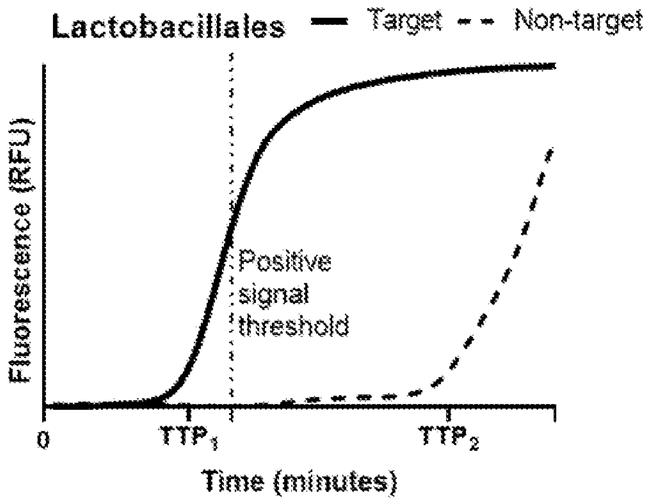
Figure 1F:
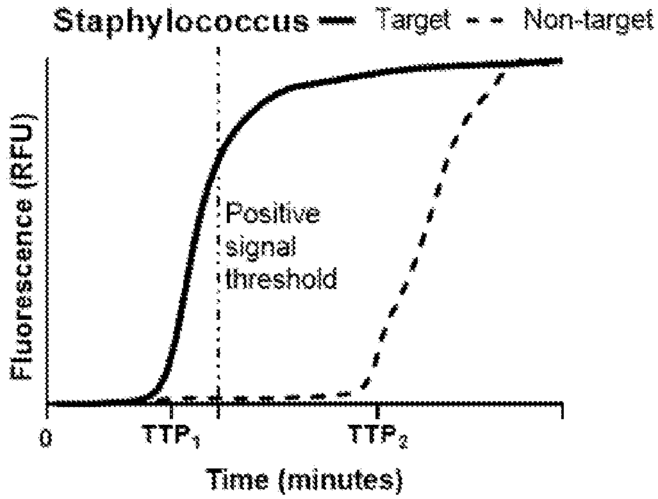

Each target organism belonging to the gram-negative primer sets (*Acinetobacter*, Enterobacterales, Pasteurellales and Pseudomonadales, FIGS. 1A-1D) amplified before the established threshold, thus indicating significant amounts of bacterial genomes present in the sample. Conversely, when a representative non-target genome was tested with the gram-negative primer sets, amplification after the established threshold or no amplification was observed. The same behavior was observed in the gram-positive primer sets (Lactobacillales and *Staphylococcus*, FIGS. 1E and 1F) where target genomes also amplified before the established threshold, and a representative non-target genome amplified after the established threshold.

Figure 2A:
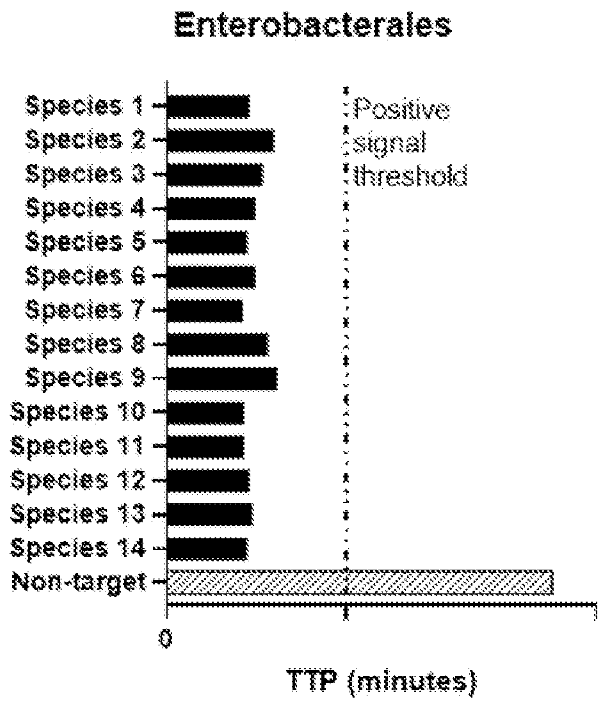
FIGS. 2A-2C show examples of three primer sets and the number of targeted species covered. To be cost- and time-effective, the primer sets were designed to encompass as many species as possible.
Figure 2B:
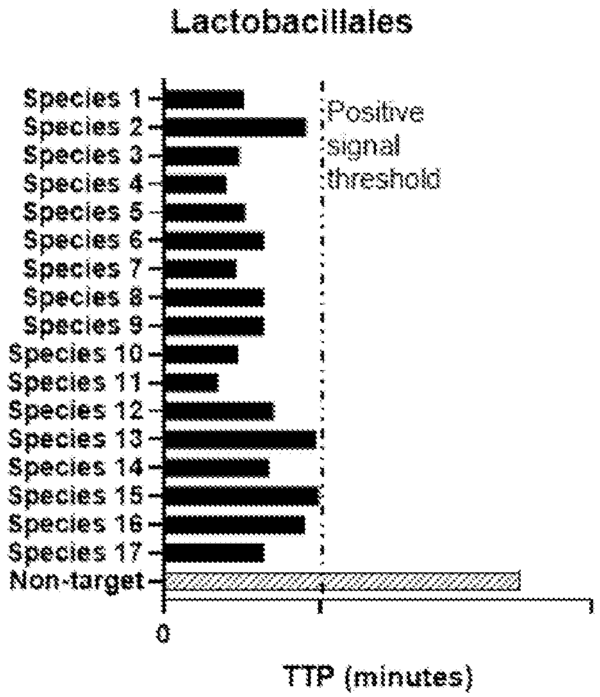
Figure 2C:
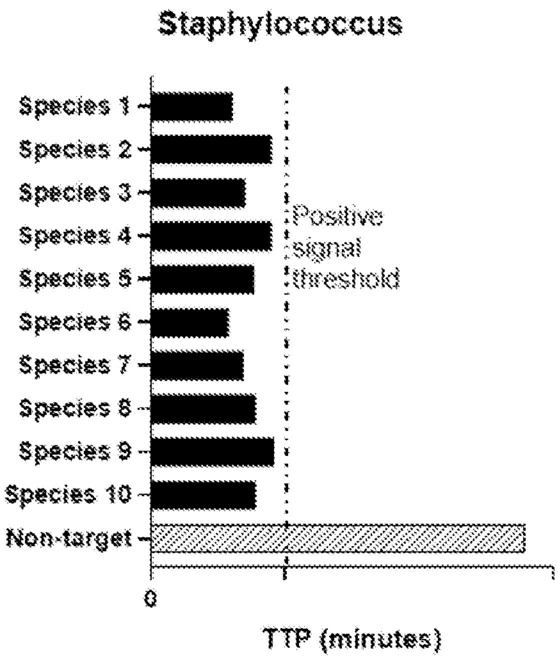

Because the primer sets described herein encompass a broad number of targets, a single primer set can be used for the detection of multiple bacteria. This is illustrated in FIGS. 2A-2C with three example primer sets: Enterobacterales (FIG. 2A), Lactobacillales (FIG. 2B), and *Staphylococcus* (FIG. 2C). The primer sets of the present invention allow for screening of the major causative bacterial pathogens in bloodstream infections with high confidence (e.g., high negative predictive value (NPV)), either as a standalone platform or in tandem with other molecular- or sequencing-based tests, such as whole genome sequencing and/or whole genome amplification. Though the bacteria in the tested samples were of a known origin and quantity, it should be understood that, in practice, clinical samples obtained from subjects will contain bacteria of unknown origin and quantity. The primer sets disclosed herein allow for the identification of these unknown bacteria present in a clinical sample.

In some embodiments, after a clinical sample has been processed according to the methods of U.S. Pat. No. 10,544,446, a molecular-based enrichment method (e.g., whole genome amplification (WGA)) may be performed towards quantification by next-generation sequencing (NGS) for bacterial species identification by k-mer matching and Antimicrobial Resistance Sensitivity (AMR/S) predictions. In some embodiments, the methods disclosed herein are performed after the molecular-based enrichment method (e.g., WGA).

Figure 3A:
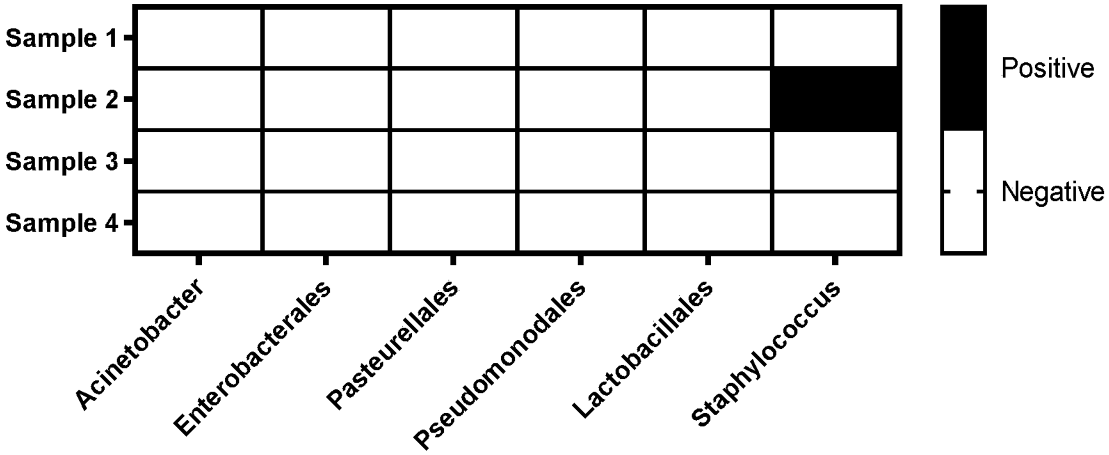
FIGS. 3A and 3B show examples of the output data obtained using the methods of the present invention. Blood was spiked with a known quantity of *Staphylococcus lugduensis* cells and processed similarly to the sample processing method described in U.S. Pat. No. 10,544,446 to both remove human cells and decrease SPS carry over. After human DNA depletion and sample concentration, the sample was then subjected to the REPLI-g Single Cell protocol (Qiagen Cat. #150345) to lyse the collected cells and amplify the resulting DNA for 4 hours. The time-to-positive (TTP) was calculated to verify the presence of bacteria in each sample, and was compared against an established threshold to determine a positive (bacteria-containing) or negative (bacteria non-containing) result. The same samples were later quantified with next generation sequencing (NGS) data using the metric MB_species, which quantifies the total number of sequenced megabases determined to have originated from the spike-in bug, *Staphylococcus lugdunensis*.
Figure 3B:
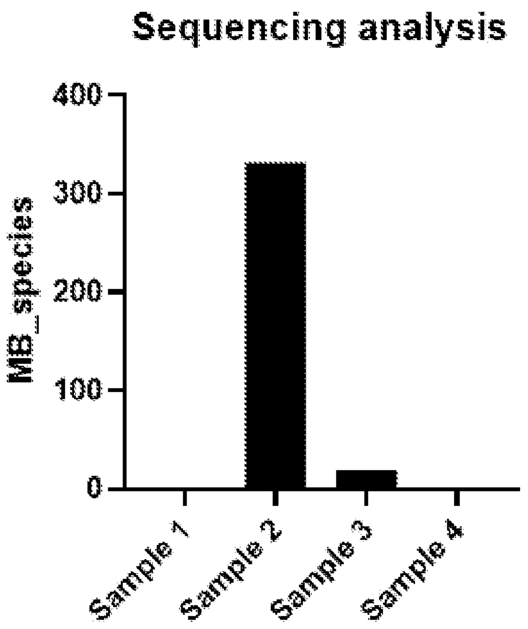

In FIGS. 3A and 3B, four samples were diluted and then assayed using all six primer sets to determine the presence of bacterial genomes. Upon calculating TTPs for each primer set using the pre-established cutoff, it was determined whether samples were positive or negative. Of the four samples, only Sample 2 showed a positive signal, calculated as described above. The positive signal observed in Sample 2 was later confirmed with sequencing tests to contain a significant amount of bacterial DNA.

An established threshold can be set to determine the sensitivity of the assay for samples of a given amount of bacterial DNA. The data in this Example sets a high established threshold; that is, only samples containing more than 20 megabases (e.g., 20 MB_species or greater) of the specific bacterial DNA of interest were designated as positive samples. However, it should be noted that the TTP threshold can be adjusted to higher or lower established thresholds to encompass a wider range of bacterial DNA concentrations, which may be specific to individual applications.

Figure 4:
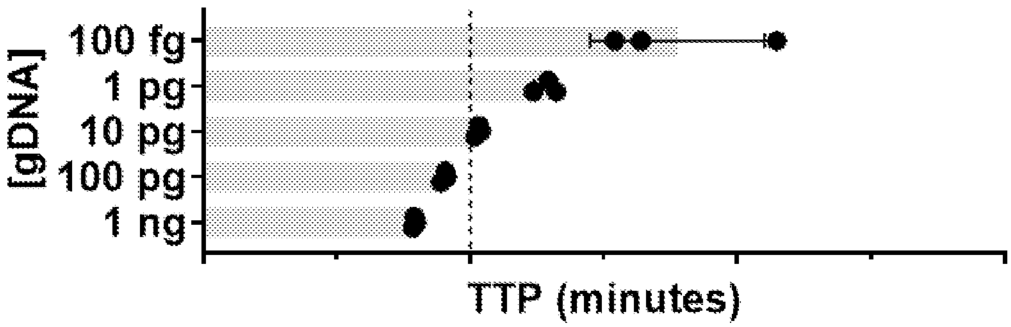
FIG. 4 shows an example of performance data obtained using the methods of the present invention in combination with a purified gDNA sample. Ten-fold dilutions of *Staphylococcus aureus* purified gDNA were assayed using the *Staphylococcus* primer set. The established threshold (dashed line) can be set to determine the sensitivity of the assay for samples of a given amount of bacterial DNA. For example, the established threshold shown in FIG. 4 designates samples with at least 10 μg of genomic DNA as positive samples. However, it should be noted that the established threshold can be modified to encompass a narrower or wider range of genomic DNA quantities, which may be specific to individual applications.

For example, FIG. 4 shows performance data obtained using the methods of the present invention in combination with a purified gDNA sample. Ten-fold dilutions of *Staphylococcus aureus* purified gDNA were assayed using the *Staphylococcus* primer set. The established threshold (dashed line) designates samples with at least 10 μg of genomic DNA as positive samples.

Example 2—Demonstration of Optimized LAMP Primers on Clinical Samples

The ability of the designed LAMP primer sets described herein to detect target bacteria in clinical samples obtained from human subjects was assessed.

The 6 primer sets from Table 1 were tested as described in Example 1 against enriched DNA from three clinical samples, hereby referred to as clinical sample 1, clinical sample 2, and clinical sample 3. Clinical samples were collected from patients with suspected or diagnosed blood stream infections, split into 4 subsamples per clinical sample, and processed according to the methods of U.S. Pat. No. 10,544,446, a molecular-based enrichment method.

Figure 5A:
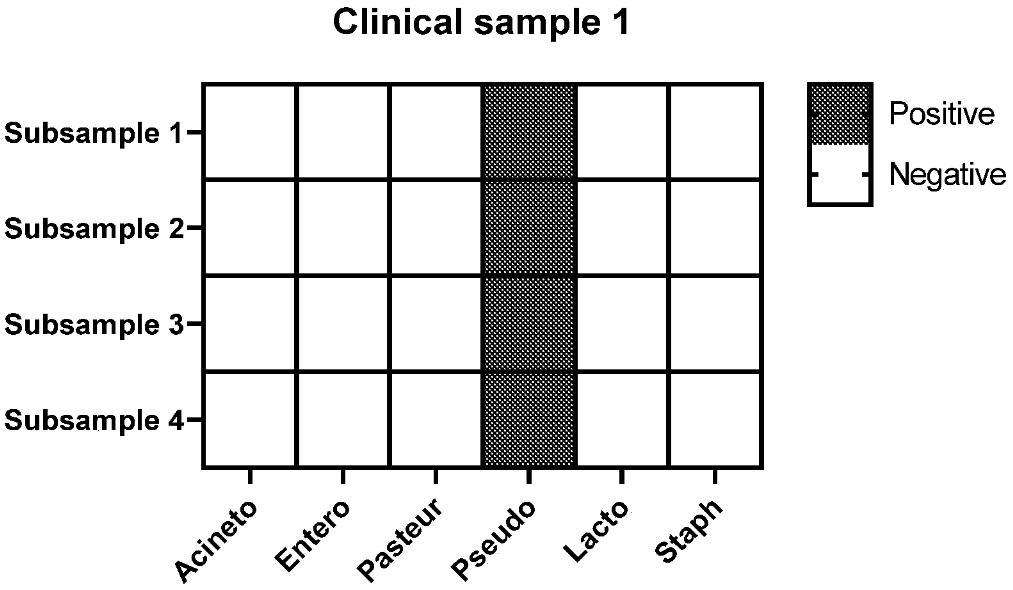
FIGS. 5A-5C show examples of bacterial genome detection, using the nucleic acid primer sets described herein, in clinical samples obtained from human subjects. Each clinical sample was split into four subsamples. Positive reaction signal, which indicates the presence of bacteria, is determined by amplification (as measured by relative fluorescent units, RFU) before a predetermined time threshold, which is set for each specific primer group.
Figure 5B:
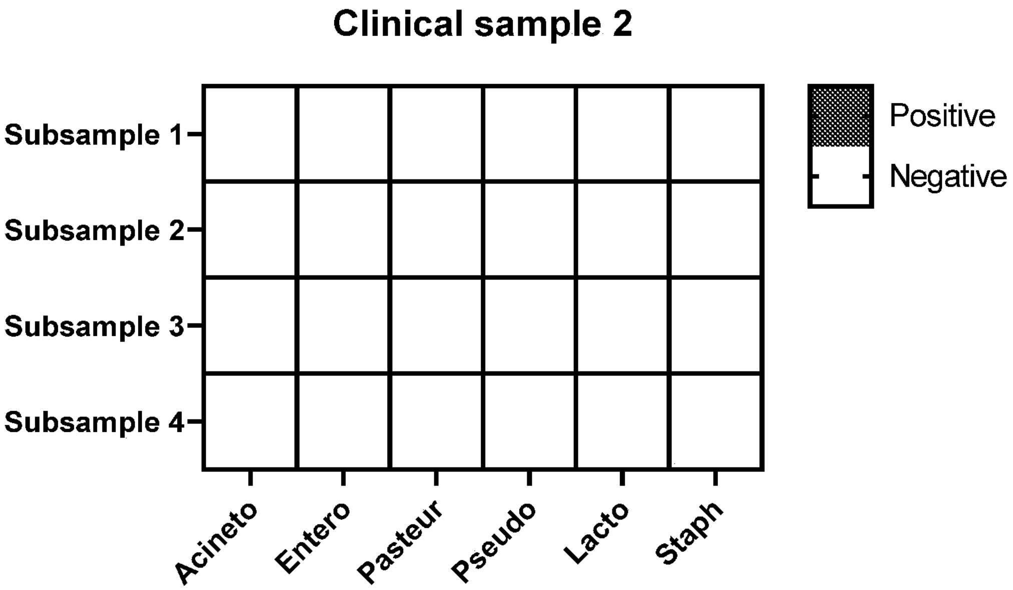
Figure 5C:
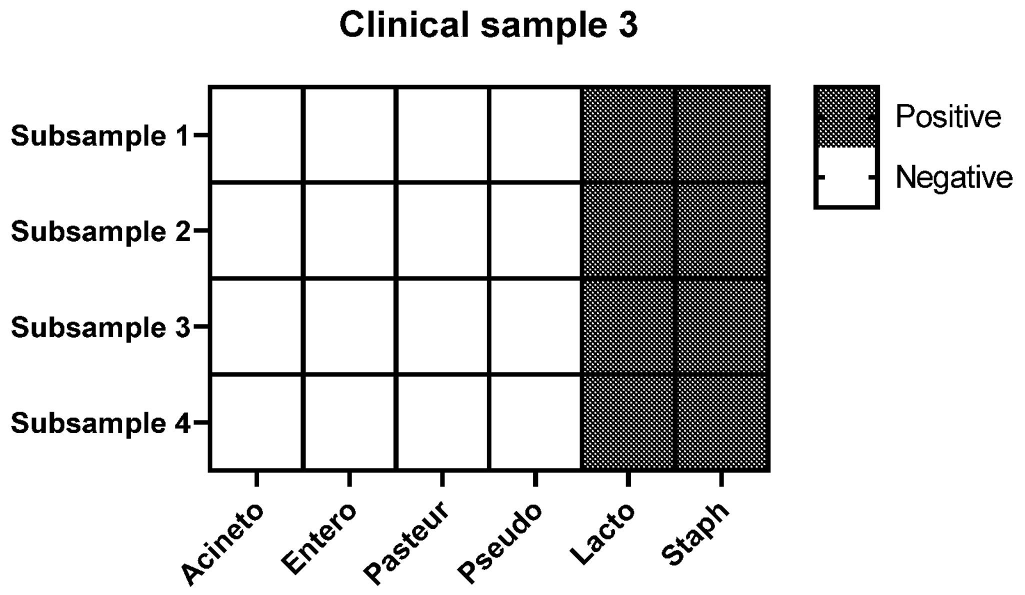
Figure 6A:
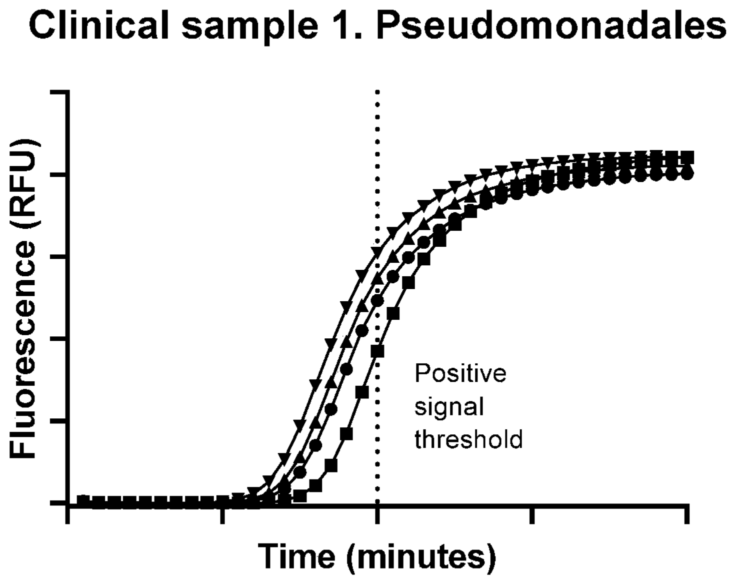
FIGS. 6A and 6B show the detection of Pseudomonadales and *Staphylococcus* in a first clinical sample. Positive reaction signal, which indicates the presence of bacteria, is determined by amplification (as measured by relative fluorescent units, RFU) before a predetermined time threshold, which is set for each specific primer group.
Figure 6B:
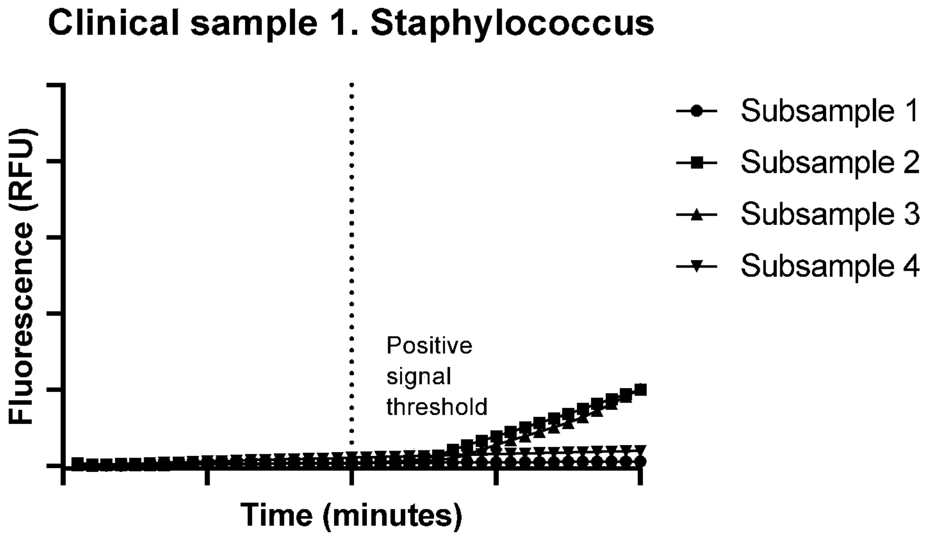
Figure 7A:
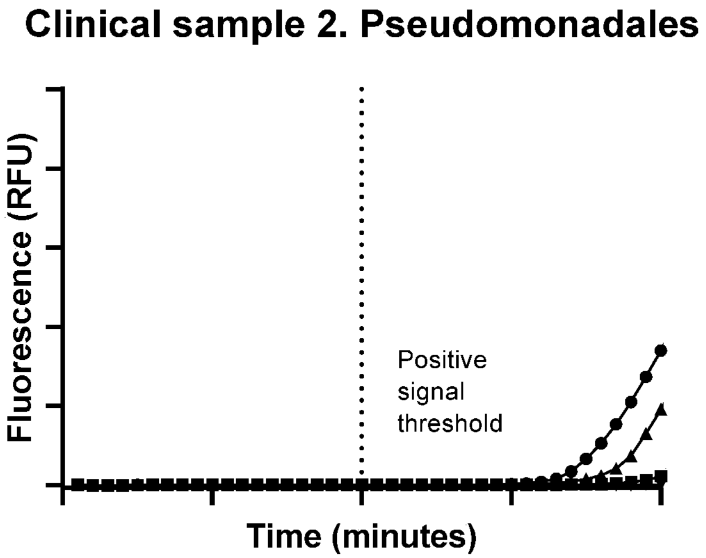
FIGS. 7A and 7B show the detection of Pseudomonadales and *Staphylococcus* in a second clinical sample. Positive reaction signal, which indicates the presence of bacteria, is determined by amplification (as measured by relative fluorescent units, RFU) before a predetermined time threshold, which is set for each specific primer group.
Figure 7B:
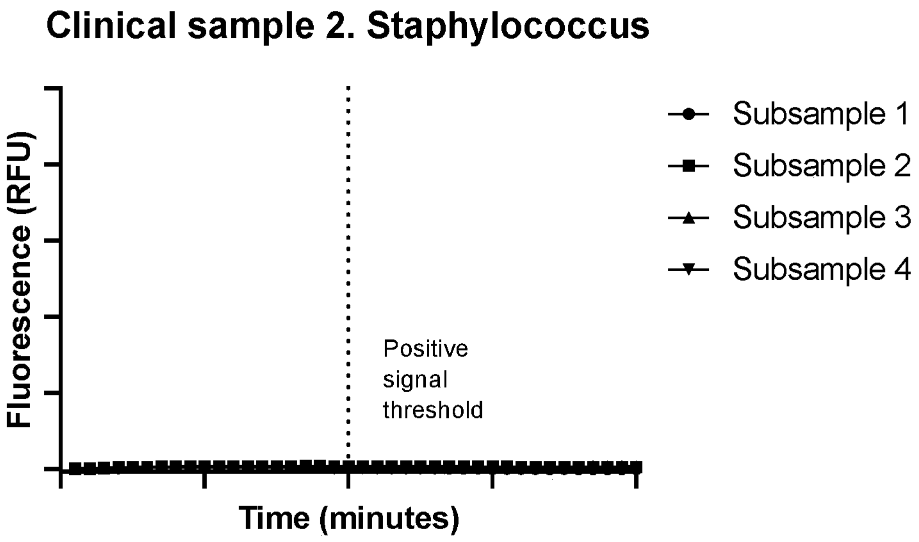
Figure 8A:
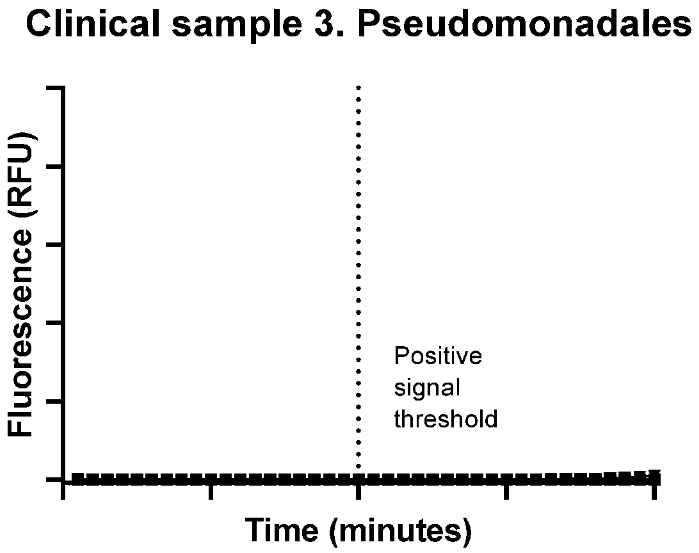
FIGS. 8A and 8B show the detection of Pseudomonadales and *Staphylococcus* in a third clinical sample. Positive reaction signal, which indicates the presence of bacteria, is determined by amplification (as measured by relative fluorescent units, RFU) before a predetermined time threshold, which is set for each specific primer group.
Figure 8B:
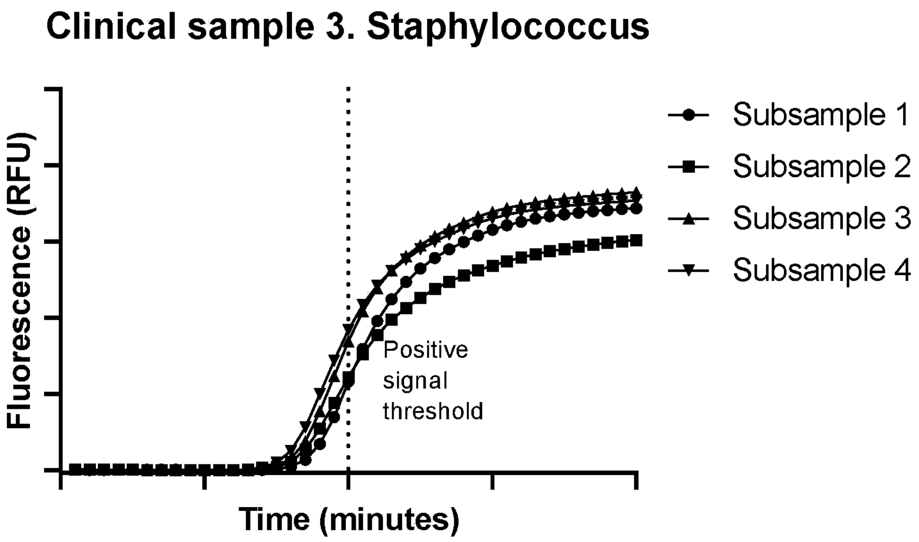

Of the 6 primer sets tested, clinical sample 1 tested positive for Pseudomonadales, clinical sample 2 did not test positive for any of the target bacteria, and clinical sample 3 tested positive for both Lactobacillales and *Staphylococcus* (FIGS. 5A-5C, respectively). Positive reaction signal is determined by amplification (as measured by relative fluorescent units, RFU) before a predetermined time threshold, which is set for each specific primer group. For the Pseudomonadales and *Staphylococcus* primer sets, fluorescence (RFU) graphed against time (minutes) is shown in FIGS. 6A-6B, 7A-7B, and 8A-8B for all three clinical samples.

Figure 9A:
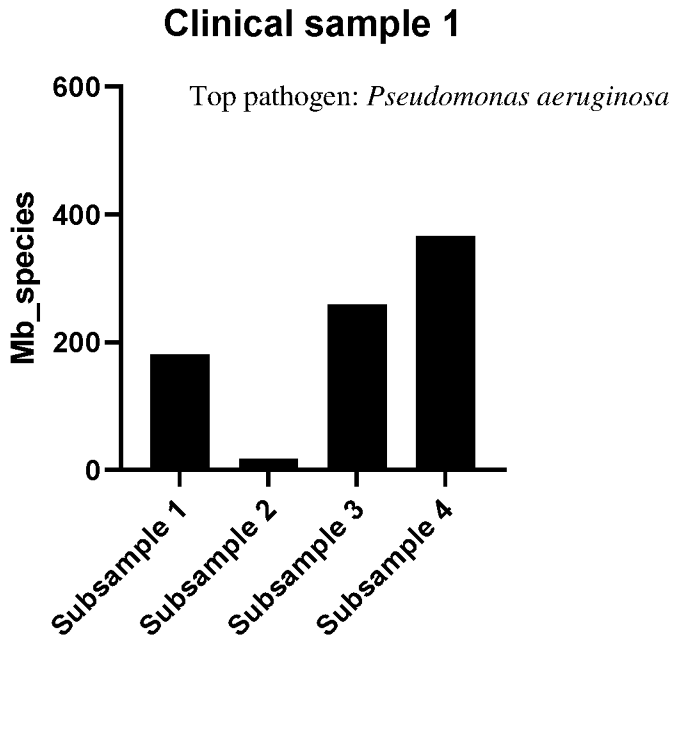
FIGS. 9A-9C show data demonstrating the top pathogen present in each of three clinical samples obtained from human subjects. The megabases (Mb) of sequencing data classified to the top pathogen species is graphed for all clinical samples.
Figure 9B:
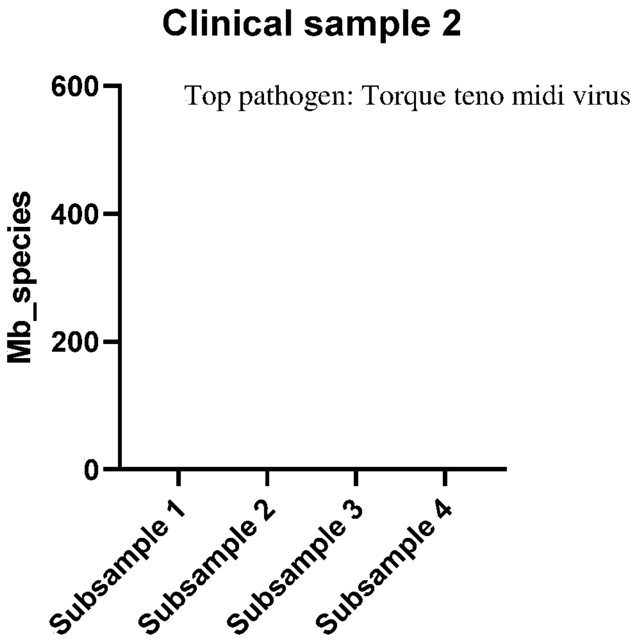
Figure 9C:
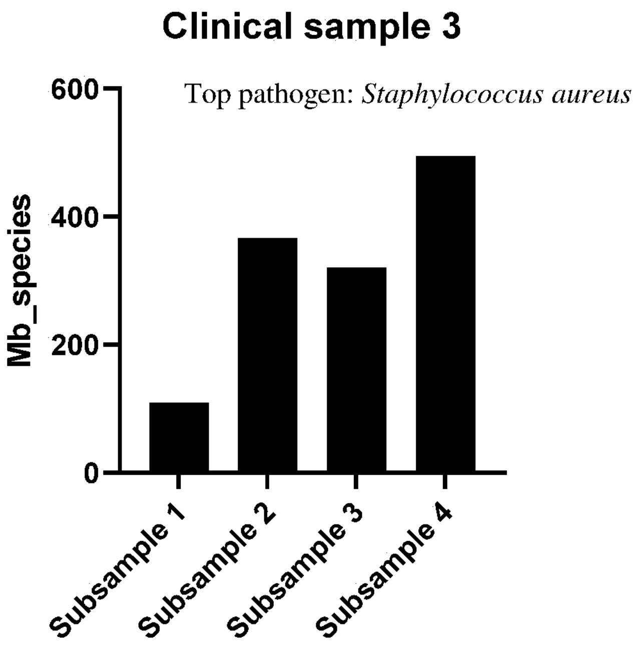

To verify the absence or presence of pathogen DNA, sequencing libraries were prepared for all clinical samples using Oxford Nanopore Technologies (ONT)'s SQK-RPB004 or SQK-LSK109 kit and sequenced on MinION Mk1B or GridION Mk1 with R9.4.1 FLO-MIN106 flowcells. Sequencing data was processed through KRAKEN software (Wood, D. E., Salzberg, S. L. (2014), Kraken: ultrafast metagenomic sequence classification using exact alignments, Genome Biol 15, R46). The megabases (Mb) of sequencing data classified to the top pathogen species is graphed in FIGS. 9A-9C for all clinical samples. Clinical sample 1's top pathogen species was *Pseudomonas aeruginosa*, with quantities ranging from 17.79 to 363.75 Mb measured in each subsample (FIG. 9A); clinical sample 2's top pathogen species was Torque teno midi virus (a non-bacterial pathogen), with quantities ranging from 0.02 to 1.69 Mb measured in each subsample (FIG. 9B); clinical sample 3's top pathogen species was *Staphylococcus aureus*, with quantities ranging from 109.34 to 494.74 Mb measured in each subsample (FIG. 9C).

Microbiologic data workup showed that clinical sample 1 had a positive blood culture identified as *Pseudomonas aeruginosa* 23 hours prior to the research blood draw. For clinical sample 2, three blood cultures taken within 24 hours before or after the research draw were negative for any bacterial pathogen. For clinical sample 3, three blood cultures taken within 24 hours before or after the research draw were positive for *Staphylococcus aureus*. These blood culture results confirm the results obtained using the LAMP primer sets of the present disclosure.

Comparison of both the sequencing (FIGS. 9A-9C) and the clinical microbiologic data show that the set of 6 LAMP primer reactions were able to positively identify clinical samples which contained bacterial DNA, which bacterial DNA could then be identified (clinical samples 1 and 3), while also successfully screening out samples which were negative for bacterial pathogens (clinical sample 2).

Although particular embodiments of the invention have been illustrated by the foregoing exemplary embodiments, it should be understood that the examples are illustrative only and not intended to be limiting. One of skill in the art will recognize that methods and materials similar or equivalent to those described herein can be used in the practice of the present invention, and numerous changes in the details of implementation of the disclosed subject matter may be made without departing from the spirit and scope of the disclosed subject matter. The scope of the invention is limited only by the claims.

We claim:

1. A set of isolated nucleic acid primers suitable for loop-mediated isothermal amplification (LAMP) and detection of a multiplicity of bacterial genomes, wherein the set is selected from the group consisting of:

a set of nucleic acid primers for detection of Lactobacillales comprising four nucleotide sequences having at least 70% identity to SEQ ID NOs: 1-4, respectively;

a set of nucleic acid primers for detection of *Staphylococcus* comprising four nucleotide sequences having at least 70% identity to SEQ ID NOs: 7-10, respectively;

a set of nucleic acid primers for detection of *Acinetobacter* comprising four nucleotide sequences having at least 70% identity to SEQ ID NOs: 13-16, respectively;

a set of nucleic acid primers for detection of Enterobacterales comprising four nucleotide sequences having at least 70% identity to SEQ ID NOs: 19-22, respectively;

a set of nucleic acid primers for detection of Pasteurellales comprising four nucleotide sequences having at least 70% identity to SEQ ID NOs: 25-28, respectively; and a set of nucleic acid primers for detection of Pseudomonadales comprising four nucleotide sequences having at least 70% identity to SEQ ID NOs: 31-34, respectively.

2. The set of nucleic acid primers of claim 1, further comprising:

(i) one or more additional nucleic acid primers for detection of Lactobacillales comprising nucleotide sequences having at least 70% identity to SEQ ID NOs: 5 and/or 6, respectively;

(ii) one or more additional nucleic acid primers for detection of *Staphylococcus* comprising nucleotide sequences having at least 70% identity to SEQ ID NOs: 11 and/or 12, respectively;

(iii) one or more additional nucleic acid primers for detection of *Acinetobacter* comprising nucleotide sequences having at least 70% identity to SEQ ID NOs: 17 and/or 18, respectively;

(iv) one or more additional nucleic acid primers for detection of Enterobacterales comprising nucleotide sequences having at least 70% identity to SEQ ID NOs: 23 and/or 24, respectively;

(v) one or more additional nucleic acid primers for detection of Pasteurellales comprising nucleotide sequences having at least 70% identity to SEQ ID NOs: 29 and/or 30, respectively; and/or (vi) one or more additional nucleic acid primers for detection of Pseudomonadales comprising nucleotide sequences having at least 70% identity to SEQ ID NOs: 35 and/or 36, respectively.

3. The set of nucleic acid primers of claim 1, wherein:

(i) the Lactobacillales are one or more bacterial species selected from the group consisting of *Bacillus cereus, Enterococcus avium, Enterococcus casseliflavus, Enterococcus faecalis, Enterococcus faecium, Enterococcus gallinarum, Enterococcus raffinosus, Lactobacillus rhamnosus, Listeria monocytogenes, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and *Streptococcus sanguinis;*

(ii) the *Staphylococcus* are one or more bacterial species selected from the group consisting of *Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans*, and *Staphylococcus warneri;*

(iii) the *Acinetobacter* are one or more bacterial species selected from the group consisting of *Acinetobacter ursingii* and *Acinetobacter baumannii;*

(iv) the Enterobacterales are one or more bacterial species selected from the group consisting of: *Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Klebsiella aerogenes, Klebsiella oxytoca, Klebsiella pneumoniae, Morganella morganii Pantoea agglomerans, Proteus mirabilis, Raoultella ornithinolytica, Salmonella enterica, Serratia liquefaciens*, and *Serratia marcescens;*

(v) the Pasteurellales are one or more bacterial species selected from the group consisting of *Haemophilus influenzae* and *Pasteurella multocida*; and/or (vi) the Pseudomonadales are one or more bacterial species selected from the group consisting of *Acinetobacter ursingii, Acinetobacter baumannii, Pseudomonas aeruginosa, Pseudomonas putida*, and *Stenotrophomonas maltophilia.*

4. The set of nucleic acid primers of claim 1, wherein each nucleic acid primer comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID Nos: 1-4, 7-10, 13-16, 19-22, 25-28, or 31-34, respectively.

5. The set of nucleic acid primers of claim 1, wherein each nucleic acid primer comprises a nucleotide sequence that does not have any consecutive nucleotide substitutions relative to SEQ ID NOs: 1-4, 7-10, 13-16, 19-22, 25-28, or 31-34, respectively.

6. The set of nucleic acid primers of claim 1, wherein each nucleic acid primer comprises a nucleotide sequence that does not have any nucleotide substitutions relative to SEQ ID NOs: 1-4, 7-10, 13-16, 19-22, 25-28, or 31-34, respectively, within the last 5, 6, or 7 nucleotides of the 3' end of the nucleotide sequence.

7. The set of nucleic acid primers of claim 1, wherein the primers mediate amplification of one or more conserved regions of the bacterial genomes, wherein the one or more conserved regions comprise a 16S rRNA gene sequence.

8. The set of nucleic acid primers of claim 1, wherein the multiplicity of bacterial genomes comprises genomes from two or more bacterial species within Lactobacillales, *Staphylococcus, Acinetobacter, Enterobacterales, Pasteurellas*, and *Pseudomonadales.*

9. A multiplicity of sets of isolated nucleic acid primers suitable for loop-mediated isothermal amplification (LAMP) and detection of a multiplicity of bacterial genomes, wherein the multiplicity of sets comprises at least two sets of nucleic acid primers selected from the group consisting of the set according to claim 1.

10. A multiplicity of sets of isolated nucleic acid primers suitable for loop-mediated isothermal amplification (LAMP) and detection of a multiplicity of bacterial genomes, wherein the multiplicity of sets of nucleic acid primers comprises at least two sets selected from the group consisting of:

a set of nucleic acid primers for detection of Lactobacillales comprising four nucleotide sequences having at least 70% identity to SEQ ID NOs: 1-4, respectively;

a set of nucleic acid primers for detection of *Staphylococcus* comprising four nucleotide sequences having at least 70% identity to SEQ ID NOs: 7-10, respectively;

a set of nucleic acid primers for detection of *Acinetobacter* comprising four nucleotide sequences having at least 70% identity to SEQ ID NOs: 13-16, respectively;

a set of nucleic acid primers for detection of Enterobacterales comprising four nucleotide sequences having at least 70% identity to SEQ ID NOs: 19-22, respectively;

a set of nucleic acid primers for detection of Pasteurellales comprising four nucleotide sequences having at least 70% identity to SEQ ID NOs: 25-28, respectively; and a set of nucleic acid primers for detection of Pseudomonadales comprising four nucleotide sequences having at least 70% identity to SEQ ID NOs: 31-34, respectively.

11. The multiplicity of sets of isolated nucleic acid primers of claim 10, wherein:

(i) the set of nucleic acid primers for detection of Lactobacillales further comprises one or more nucleic acid primers comprising nucleotide sequences having at least 70% identity to SEQ ID NOs: 5 and/or 6, respectively;

(ii) the set of nucleic acid primers for detection of *Staphylococcus* further comprises one or more nucleic acid primers comprising nucleotide sequences having at least 70% identity to SEQ ID NOs: 11 and/or 12, respectively;

(iii) the set of nucleic acid primers for detection of *Acinetobacter* further comprises one or more nucleic acid primers comprising nucleotide sequences having at least 70% identity to SEQ ID NOs: 17 and/or 18, respectively;

(iv) the set of nucleic acid primers for detection of Enterobacterales further comprises one or more nucleic acid primers comprising nucleotide sequences having at least 70% identity to SEQ ID NOs: 23 and/or 24, respectively;

(v) the set of nucleic acid primers for detection of Pasteurellales further comprises one or more nucleic acid primers comprising nucleotide sequences having at least 70% identity to SEQ ID NOs: 29 and/or 30, respectively; and/or (vi) the set of nucleic acid primers for detection of Pseudomonadales further comprises one or more nucleic acid primers comprising nucleotide sequences having at least 70% identity to SEQ ID NOs: 35 and/or 36, respectively.

12. The multiplicity of sets of isolated nucleic acid primers of claim 10, wherein:

(i) the Lactobacillales are one or more bacterial species selected from the group consisting of *Bacillus cereus, Enterococcus avium, Enterococcus casseliflavus, Enterococcus faecalis, Enterococcus faecium, Enterococcus gallinarum, Enterococcus raffinosus, Lactobacillus rhamnosus, Listeria monocytogenes, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and *Streptococcus sanguinis;*

(ii) the *Staphylococcus* are one or more bacterial species selected from the group consisting of *Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans*, and *Staphylococcus warneri;*

(iii) the *Acinetobacter* are one or more bacterial species selected from the group consisting of *Acinetobacter ursingii* and *Acinetobacter baumannii;*

(iv) the Enterobacterales are one or more bacterial species selected from the group consisting of *Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Klebsiella aerogenes, Klebsiella oxytoca, Klebsiella pneumoniae, Morganella morganii Pantoea*

*agglomerans, Proteus mirabilis, Raoultella ornithinolytica, Salmonella enterica, Serratia liquefaciens*, and *Serratia marcescens;*

(v) the Pasteurellales are one or more bacterial species selected from the group consisting of *Haemophilus influenzae* and *Pasteurella multocida*; and/or (vi) the Pseudomonadales are one or more bacterial species selected from the group consisting of *Acinetobacter ursingii, Acinetobacter baumannii, Pseudomonas aeruginosa, Pseudomonas putida*, and *Stenotrophomonas maltophilia.*

13. The multiplicity of sets of claim 10, wherein at least one set of the multiplicity of sets further comprises one or more additional isolated nucleic acid primers suitable for LAMP and detection of a multiplicity of bacterial genomes.

14. The multiplicity of sets of nucleic acid primers of claim 10, wherein each nucleic acid primer comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 1-4, 7-10, 13-16, 19-22, 25-28, or 31-34, respectively.

15. The multiplicity of sets of nucleic acid primers of claim 10, wherein the primers mediate amplification of one or more conserved regions of the bacterial genome, wherein the one or more conserved regions comprise a 16S rRNA gene sequence.

16. A method for detecting a multiplicity of bacterial genomes, the method comprising:

(a) providing a reaction mixture comprising at least one set of isolated nucleic acid primers suitable for loop-mediated isothermal amplification (LAMP) and detection of a multiplicity of bacterial genomes according to claim 1, dNTPs, a DNA polymerase, and a DNA sample to be tested for the presence of bacterial nucleic acids;

(b) subjecting the reaction mixture to LAMP amplification reaction conditions to produce amplified bacterial nucleic acids; and (c) detecting the amplified bacterial nucleic acids.

17. A kit comprising a multiplicity of sets of isolated nucleic acid primers suitable for loop-mediated isothermal amplification (LAMP) and detection of a multiplicity of bacterial genomes, wherein the multiplicity of sets comprises at least two sets of nucleic acid primers selected from the set of isolated nucleic acid primers suitable for loop-mediated isothermal amplification (LAMP) and detection of a multiplicity of bacterial genomes according to claim 1.

18. The kit of claim 17, wherein the multiplicity of bacterial genomes comprises genomes from two or more bacterial species selected from the group consisting of *Acinetobacter ursingii, Acinetobacter baumannii, Bacillus cereus, Citrobacter freundii, Citrobacter koseri, Enterobacter cloacae, Enterococcus avium, Enterococcus casseliflavus, Enterococcus faecalis, Enterococcus faecium, Enterococcus gallinarum, Enterococcus raffinosus, Escherichia coli, Haemophilus influenzae, Klebsiella aerogenes, Klebsiella oxytoca, Klebsiella pneumoniae, Lactobacillus rhamnosus, Listeria monocytogenes, Morganella morganii, Pantoea agglomerans, Pasteurella multocida, Proteus mirabilis, Pseudomonas aeruginosa, Pseudomonas putida, Raoultella ornithinolytica, Salmonella enterica, Serratia liquefaciens, Serratia marcescens, Staphylococcus aureus, Staphylococcus capitis, Staphylococcus caprae, Staphylococcus epidermidis, Staphylococcus haemolyticus, Staphylococcus hominis, Staphylococcus lugdunensis, Staphylococcus saprophyticus, Staphylococcus simulans, Staphylococcus warneri, Stenotrophomonas maltophilia, Streptococcus agalactiae, Streptococcus anginosus, Streptococcus constellatus, Streptococcus dysgalactiae, Streptococcus intermedius, Streptococcus mutans, Streptococcus oralis, Streptococcus parasanguinis, Streptococcus pneumoniae, Streptococcus pyogenes, Streptococcus salivarius*, and *Streptococcus sanguinis.*

19. A method of detecting a multiplicity of bacterial genomes, the method comprising:

(i) providing a reaction mixture comprising at least two sets of isolated nucleic acid primers suitable for loop-mediated isothermal amplification (LAMP) and detection of a multiplicity of bacterial genomes according to claim 1;

(ii) further providing to the reaction mixture of (i), a DNA polymerase, dNTPs, and DNA sample to be tested for the presence of bacterial nucleic acids;

(iii) subjecting the reaction mixture of (ii) to LAMP amplification reaction conditions to produce multiplicity of amplified bacterial nucleic acids; and (iv) detecting the multiplicity of amplified bacterial nucleic acids.

* * * * *

SEQUENCE LISTING

```
<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
```

gtggggagca aacaggatt 19

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tcttcgcgtt gcttcgaatt 20

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3
tgcgttagct gcggcactaa ggtccacgcc gtaaacgatg 40

<210> SEQ ID NO 4
<211> LENGTH: 38
<212> TYPE: DNA
<213> ORGANISM: Artificial Sequence
<220> FEATURE:
<223> OTHER INFORMATION: Synthetic

<400> SEQUENCE: 4
cctggggagt acgaccgcaa catgctccac cgcttgtg 38

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
cggaaagggc ctaacaccta gc 22

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
ggttgaaact caaaggaatt gacg 24

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gcgcagagat atggaggaac 20

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
aggcggagtg cttaatgc 18

<210> SEQ ID NO 9
<211> LENGTH: 40
<212> TYPE: DNA
<213> ORGANISM: Artificial Sequence
<220> FEATURE:
<223> OTHER INFORMATION: Synthetic

<400> SEQUENCE: 9
tcctgtttga tccccacgct ttggcgaagg cgactttctg 40

<210> SEQ ID NO 10
<211> LENGTH: 40
<212> TYPE: DNA
<213> ORGANISM: Artificial Sequence
<220> FEATURE:
<223> OTHER INFORMATION: Synthetic

<400> SEQUENCE: 10
agataccctg gtagtccacg cccactaagg ggcggaaacc 40

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
cgcacatcag cgtcagttac aga 23

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
taaacgatga gtgctaagtg ttagg 25

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
accgcatacg tcctacgg 18

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
ggttcccccc attgtcca 18

<210> SEQ ID NO 15
<211> LENGTH: 42
<212> TYPE: DNA
<213> ORGANISM: Artificial Sequence
<220> FEATURE:
<223> OTHER INFORMATION: Synthetic

<400> SEQUENCE: 15
gcctttaccc caccaactag ctgagaaagc aggggatctt cg 42

<210> SEQ ID NO 16
<211> LENGTH: 41
<212> TYPE: DNA
<213> ORGANISM: Artificial Sequence
<220> FEATURE:
<223> OTHER INFORMATION: Synthetic

<400> SEQUENCE: 16
tgtagcgggt ctgagaggat gatattcccc actgctgcct c 41

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
gctcatctat tagcgcaagg tc 22

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
agacacggcc cagactccta 20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
agtcttgtag agggggtag 20

<210> SEQ ID NO 20
<211> LENGTH: 18
<212> TYPE: DNA
<213> ORGANISM: Artificial Sequence
<220> FEATURE:
<223> OTHER INFORMATION: Synthetic

<400> SEQUENCE: 20
cgttagctcc ggaagcca 18

<210> SEQ ID NO 21
<211> LENGTH: 40
<212> TYPE: DNA
<213> ORGANISM: Artificial Sequence
<220> FEATURE:
<223> OTHER INFORMATION: Synthetic

<400> SEQUENCE: 21
cagtctttgt ccagggggcc aattccaggt gtagcggtga 40

<210> SEQ ID NO 22
<211> LENGTH: 40
<212> TYPE: DNA
<213> ORGANISM: Artificial Sequence
<220> FEATURE:
<223> OTHER INFORMATION: Synthetic

<400> SEQUENCE: 22
gctcaggtgc gaaagcgtgg acctccaagt cgacatcgtt 40

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
ccaccggtat tcctccagat ctcta 25

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
taccctggta gtccacgccg 20

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
tccacgtgta gcggtgaa 18

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ttatcacgtt agcttcgggc 20

<210> SEQ ID NO 27
<211> LENGTH: 42
<212> TYPE: DNA
<213> ORGANISM: Artificial Sequence
<220> FEATURE:
<223> OTHER INFORMATION: Synthetic

<400> SEQUENCE: 27
agcgtcagta cattcccaag ggatgcgtag agatgtggag ga 42

<210> SEQ ID NO 28

<211> LENGTH: 40
<212> TYPE: DNA
<213> ORGANISM: Artificial Sequence
<220> FEATURE:
<223> OTHER INFORMATION: Synthetic

<400> SEQUENCE: 28
gcgaaagcgt ggggagcaaa ccaatcccca aatcgacagc 40

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
gctgccttcg ccttcggta 19

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
aggattagat accctggtag tcca 24

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
gaaagcaggg gatcttcgg 19

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
accttcttca cacacgcg 18

<210> SEQ ID NO 33
<211> LENGTH: 42
<212> TYPE: DNA
<213> ORGANISM: Artificial Sequence
<220> FEATURE:
<223> OTHER INFORMATION: Synthetic

<400> SEQUENCE: 33
accagttacg gatcgtcgcc ttatcagatg agcctaggtc gg 42

<210> SEQ ID NO 34
<211> LENGTH: 40
<212> TYPE: DNA
<213> ORGANISM: Artificial Sequence
<220> FEATURE:
<223> OTHER INFORMATION: Synthetic

<400> SEQUENCE: 34

-continued

```
cacactggaa ctgagacacg gtggctttcg cccattgtcc                         40


<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35

gcctttaccc caccaactag ctaat                                         25


<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36

actcctacgg gaggcagcag                                               20
```